US010959443B2

(12) United States Patent
Liao et al.

(10) Patent No.: US 10,959,443 B2
(45) Date of Patent: *Mar. 30, 2021

(54) DEVICE FOR UV-LED LIQUID MONITORING AND TREATMENT

(71) Applicant: LARQ, INC., Foster City, CA (US)

(72) Inventors: Yitao Liao, Foster City, CA (US);
Robert Walker, Foster City, CA (US);
Doug Collins, Foster City, CA (US)

(73) Assignee: LARQ, INC., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/741,004

(22) Filed: Jan. 13, 2020

(65) Prior Publication Data

US 2020/0146306 A1 May 14, 2020

Related U.S. Application Data

(63) Continuation of application No. 15/625,986, filed on Jun. 16, 2017, now Pat. No. 10,561,156, which is a
(Continued)

(30) Foreign Application Priority Data

Jun. 30, 2016 (CN) .......................... 201620683962.6

(51) Int. Cl.
*A23C 3/07* (2006.01)
*G01N 21/33* (2006.01)
(Continued)

(52) U.S. Cl.
CPC .............. *A23C 3/076* (2013.01); *A23C 9/206* (2013.01); *A23L 2/50* (2013.01); *A23L 3/28* (2013.01);
(Continued)

(58) Field of Classification Search
CPC .. C02F 1/00; C02F 1/001; C02F 1/008; C02F 1/004; C02F 1/325; C02F 1/725;
(Continued)

(56) References Cited

U.S. PATENT DOCUMENTS 6,182,453 B1 2/2001 Forsberg et al.
6,447,721 B1 9/2002 Horton, III et al.
(Continued)

FOREIGN PATENT DOCUMENTS

| CN | 102557350 A | 7/2012 |
|---|---|---|
| CN | 104768876 A | 7/2015 |
| CN | 105121357 A | 12/2015 |

OTHER PUBLICATIONS

USPTO; Non-Final Office Action dated Apr. 9, 2019 in U.S. Appl. No. 16/299,023.
(Continued)

*Primary Examiner* — Robert Clemente
*Assistant Examiner* — Akash K Varma
(74) *Attorney, Agent, or Firm* — Arc IP Law, PC; Joseph J. Mayo

(57) ABSTRACT

A liquid treatment device includes a base with a power source, a UV-LED module for providing UV-B or UV-C light to liquid, an LED for providing visible light, and a processor for selectively powering the UV-LED module and the LED, and having a UV transmissive material above the UV-LED module for allowing the UV-B or UV-C band light from the UV-LED module to be transmitted from the base housing, and a liquid storage housing removably coupled to the base housing with a storage portion configured to hold liquid and having a bottom portion comprising a UV transmissive material for allowing the UV-B or UV-C band light
(Continued)

from the UV-LED module to be transmitted into the liquid, and an output coupled for restricting outflow of the liquid from the storage portion.

20 Claims, 19 Drawing Sheets

Related U.S. Application Data continuation-in-part of application No. 15/462,721, filed on Mar. 17, 2017, now Pat. No. 10,570,028, which is a continuation-in-part of application No. 14/672,077, filed on Mar. 27, 2015, now Pat. No. 10,214,431.

(51) Int. Cl.

| | | |
|---|---|---|
| *G01N 33/18* | (2006.01) | |
| *C02F 1/00* | (2006.01) | |
| *A23L 3/28* | (2006.01) | |
| *A23L 2/50* | (2006.01) | |
| *A23C 9/20* | (2006.01) | |
| *C02F 1/32* | (2006.01) | |
| *C02F 1/72* | (2006.01) | |
| *G01N 21/53* | (2006.01) | |
| *G01N 21/64* | (2006.01) | |
| *G01N 21/94* | (2006.01) | |
| *C02F 1/28* | (2006.01) | |
| *C02F 1/44* | (2006.01) | |

(52) U.S. Cl.
CPC .............. *C02F 1/003* (2013.01); *C02F 1/008* (2013.01); *C02F 1/325* (2013.01); *C02F 1/725* (2013.01); *G01N 21/33* (2013.01); *G01N 21/53* (2013.01); *G01N 21/6486* (2013.01); *G01N 21/94* (2013.01); *G01N 33/18* (2013.01); *A23V 2002/00* (2013.01); *C02F 1/283* (2013.01); *C02F 1/44* (2013.01); *C02F 2201/009* (2013.01); *C02F 2201/326* (2013.01); *C02F 2201/3222* (2013.01); *C02F 2201/3227* (2013.01); *C02F 2209/001* (2013.01); *C02F 2209/003* (2013.01); *C02F 2209/006* (2013.01); *C02F 2209/008* (2013.01); *C02F 2209/02* (2013.01); *C02F 2209/08* (2013.01); *C02F 2209/11* (2013.01); *C02F 2209/15* (2013.01); *C02F 2209/20* (2013.01); *C02F 2209/21* (2013.01); *C02F 2303/04* (2013.01); *C02F 2305/10* (2013.01); *C02F 2307/02* (2013.01); *C02F 2307/04* (2013.01); *C02F 2307/10* (2013.01); *G01N 2201/062* (2013.01); *Y02A 20/212* (2018.01); *Y02W 10/37* (2015.05)

(58) Field of Classification Search
CPC ........ C02F 1/72; C02F 1/32; C02F 2201/008; C02F 2201/009; C02F 2201/3222; C02F 2201/3227; C02F 2201/326; C02F 2209/001; C02F 2209/003; C02F 2209/008; C02F 2209/08; C02F 2209/11; C02F 2209/15; C02F 2209/20; C02F 2209/21; C02F 2209/36; A23C 9/206; A23C 3/076; A23L 2/50; A23L 3/28
USPC ......................................................... 210/93
See application file for complete search history.

(56) References Cited

U.S. PATENT DOCUMENTS

| | | |
|---|---|---|
| 7,169,311 B2 | 1/2007 | Saccomanno |
| 7,550,746 B2 | 6/2009 | Tokhtuev et al. |
| 8,191,523 B2 | 6/2012 | Clark |
| 8,529,110 B2 | 9/2013 | Yencho |
| 2002/0130069 A1* | 9/2002 | Moskoff ............... G01N 33/18 210/85 |
| 2014/0054222 A1 | 2/2014 | Clark et al. |
| 2014/0332199 A1 | 11/2014 | Gilstad et al. |
| 2015/0158741 A1 | 6/2015 | Lee et al. |

OTHER PUBLICATIONS

USPTO; Notice of Allowance dated Feb. 6, 2020 in U.S. Appl. No. 16/299,023.
USPTO Non-Final Office Action dated Jul. 13, 2017 in U.S. Appl. No. 15/462,721.
USPTO Final Office Action dated Jun. 5, 2018 in U.S. Appl. No. 15/462,721.
USPTO Non-Final Office Action dated Mar. 13, 2019 in U.S. Appl. No. 15/462,721.
USPTO Notice of Allowance dated Nov. 18, 2019 in U.S. Appl. No. 15/462,721.
USPTO Non-Final Office Action dated Dec. 2, 2016 in U.S. Appl. No. 14/672,077.
USPTO Non-Final Office Action dated Mar. 24, 2017 in U.S. Appl. No. 14/672,077.
USPTO Final Office Action dated Jan. 31, 2018 in U.S. Appl. No. 14/672,077.
USPTO Notice of Allowance dated Oct. 25, 2018 in U.S. Appl. No. 14/672,077.
USPTO; Notice of Allowance dated Oct. 11, 2019 in U.S. Appl. No. 15/625,986.

* cited by examiner

DEVICE FOR UV-LED LIQUID MONITORING AND TREATMENT

CROSS-REFERENCE TO RELATED APPLICATIONS

The present application is a continuation of, claims priority to and the benefit of, U.S. Ser. No. 15/625,986 filed Jun. 16, 2017 entitled "DEVICE FOR UV-LED LIQUID MONITORING AND TREATMENT." The '986 is a continuation-in-part of, claims priority to and the benefit of, U.S. Ser. No. 15/462,721 filed Mar. 17, 2017 entitled "DEVICE FOR UV-LED LIQUID MONITORING AND TREATMENT." The '721 is a continuation-in-part of, claims priority to and the benefit of, U.S. Ser. No. 14/672,077 filed Mar. 27, 2015 entitled "SYSTEM AND METHOD FOR UV-LED LIQUID MONITORING AND DISINFECTION" (aka U.S. Pat. No. 10,214,431 issued Feb. 26, 2019). The '986 application also claims priority to Chinese Utility Model Application No. 2016206839626 filed Jun. 30, 2016. All of these applications are incorporated herein by reference for all purposes.

BACKGROUND

The present invention relates to liquid monitoring. More specifically, embodiments of the present invention relate to a UV-LED liquid monitoring and purification systems and methods of operation.

Water suppliers periodically monitor water quality at centralized locations, such as water treatment plants, pump stations, and the like. The periodic testing is used to check whether the provided water meets certain health quality standards.

The inventors of the present invention believe that there are drawbacks to centralized testing systems including that water delivered to the end point (consumer), e.g. home, apartment, factory, or the like, may not have the same quality as provided by the supplier. Reasons for this deterioration in quality may include contamination within the distribution network (e.g. leaky pipes, pollution, sewage contamination, etc.); contamination within an end point (e.g. leaky pipes within a factory, chemicals leached from pipes, etc.); and the like. Another drawback is believed to be because water quality is not always monitored in real-time, contaminated water may be provided to consumers for some time, before the contamination is discovered.

From the above, it is desired to have a distributed water quality monitoring and treatment system without the drawbacks described above.

SUMMARY

The present invention relates to liquid treatment. More specifically, embodiments of the present invention relate to a UV-LED liquid treatment device and methods of operation. In various embodiments, the liquid may be water (e.g. tap water, bottled water, etc.), a fruit juice (e.g. orange juice, apple juice, cranberry juice, etc.), an electrolyte (e.g. Gatorade, etc.), a flavored water (e.g. soda, etc.), a soup base, milk (e.g. human, cow, soy, almond) or the like. For sake of convenience, embodiments described herein are directed to water, however, it should be understood that many other types of liquid may be treated, as described herein.

Various embodiments of the present invention include a water purification device (e.g. a water bottle, a water dispenser, an in-house water treatment system, or the like) that uses a combination of ultraviolet LEDs to kill bacteria, viruses, and spores in the incoming water. Optionally, the system includes TiO2 (Titanium Dioxide), or H2O2 (Hydrogen peroxide) to work with UV LEDs to purify water via production of reactive oxygen species via a photo catalytic oxidation process. In general, it is contemplated that unsanitary water may include water of unknown-safety, pathogen-bearing water, or other types of liquid that if consumed by a human (or other animal) could cause illness and/or death. Additionally, the unsanitary water may also include one or more chemicals (e.g. metals, volatile organic chemicals and pesticides).

In various embodiments, a system may include some or all of the following elements: a) water analysis module, b) a physical/chemical water treatment portion, c) a UV treatment portion, d) a reservoir portion d) a communication portion, e) a filtration module, f) battery module and g) driver electronics. Some systems are used to monitor and treat water incoming to a residence, facility, or the like (e.g. water treatment unit), or treat water prior to consumption or use (e.g. water pitcher or a water bottle). In some embodiments, water quality analysis is performed upon incoming water to a user. The water quality may be analyzed for chemical contaminants and/or pathogens; the water quality may be analyzed for optical transparency and/or optical absorption; the water quality may be analyzed for optical spectroscopy and/or florescence spectroscopy. In various embodiments, the water quality may also be analyzed before and after treatment. Water purification may be performed upon the water. The purification may include filtering of suspended particulates, removal or break down of chemical impurities, and/or destruction of pathogens (e.g. bacterial or viral). In some cases the purification may be tailored to the impurities that were just determined. In various embodiments, an additional analysis may be performed upon the purified water. The initial analysis of the incoming water and/or the final analysis of the treated water may be sent via the communication portion to a centralized reporting server, e.g. the water provider, a governmental agency, or other third party monitoring agency.

In various embodiments, a communication portion may include a communication system based upon Bluetooth, WiFi, 4G, 3G, NFC, RF, Ethernet, or the like. The communication portion may directly communicate to a cloud-based reporting server via WiFi, 4G, 3G, Ethernet, or the like. In other embodiments, the communication portion communicates via Bluetooth, NFC, IR, ZigBee or other rf protocol to a smart device (e.g. smart phone, home PC, smart watch, home server, or the like) having one or more specialized software applications running thereon. In various embodiments, the water data may be stored within the applications, processed and viewed by the user on the smart device. For example, the user may see time trends in the water turbidity, the types of contaminants detected in the water, and the like. In some embodiments, the data may automatically or manually uploaded to the centralized reporting server from the application. For example, the user's application may periodically upload the water quality data captured, as described herein.

In various embodiments, a centralized reporting server receives and stores water quality reports from a multitude of users in real-time or non-real time. Based upon the real-time and/or non-real time data and based upon knowledge of the water distribution network, near-real time identification of water quality problems may be determined. Causes for the water quality problems may then be investigated, and fixes to the distribution network, modifications to the outgoing water treatment, and other actions may be taken. Further, based upon knowledge of the water distribution network and the water quality reports, over time, trends in water quality may be determined. Based upon the trends, a water provider may change its water purification procedures (e.g. add additional chemical removal steps); may determine water branches having unusual contaminants, inspect the water branches, and/or repair faulty water branches; may shut-off water provided to specific branches or shut-off water from specific sources when contaminants exceed the purification capabilities; may modify conditions around aquifers and other water sources, and the like.

According to one aspect of the invention, a water treatment device is disclosed. One apparatus includes a base housing having a power source, a UV-LED module electrically coupled to the power source, wherein the UV-LED module is configured to provide UV-C band light, a plurality of LEDs electrically coupled to the power source, wherein the plurality of LEDs are configured to provide visible light, and a processor electrically coupled to the power source, the UV-LED module, and to the plurality of LEDs, wherein the processor is configured to specify parameters for power from the power source to the UV-LED module to the power source, wherein the processor is configured to specify parameters for power from the power source to the plurality of LEDs. A system may include a visual indicator portion disposed on a first top portion the base housing and optically coupled to the plurality of LEDs, wherein the visual indicator portion is configured to receive the visible light from the plurality of LEDs and is configured to provide at least a portion of the visible light outwards in a radial direction, a first physical coupling structure disposed on a second top portion of the base housing, and a first transmissive material disposed on a third top portion of the base housing above the UV-LED module, wherein the first transmissive material is configured to allow the UV-C band light from the UV-LED module to be transmitted upward from the base housing. A device may include a water storage housing removably coupled to the base housing including: a sidewall structure configured to radially confine water stored within the water storage housing, a second physical coupling structure disposed on a bottom portion of the sidewall structure, wherein the first physical coupling structure and the second physical coupling structure are together configured to allow the water storage housing to be removably coupled to the base housing, and an upper opening configured to provide input and output of water from the water storage housing.

According to another aspect of the invention, a water treatment device is disclosed. One apparatus may include a base housing having: a battery, a UV-LED module coupled to the battery and configured to provide UV-C band light in response to first power parameters during a UV sterilization process, a plurality of LEDs coupled to the battery and configured to provide visible light in response to second power parameters, and a controller coupled to the battery, the UV-LED module, and the plurality of LEDs, wherein the processor is configured to specify the second power parameters to the plurality of LEDs and configured to specify the first power parameters during the UV sterilization process. A device may include a translucent ring of material disposed upon a first top portion the base housing, wherein the visual translucent ring is configured to receive the visible light from the plurality of LEDs and is configured to provide at least a portion of the visible light outwards in a radial direction, a first coupling structure disposed above the translucent ring, and a first transmissive material disposed on a second top portion of the base housing above the UV-LED module, wherein the first transmissive material is configured to allow the UV-C band light from the UV-LED module to be transmitted upward from the UV-LED module. A system may also include a water storage housing removably coupled to the base housing having: a sidewall structure configured to radially confine water within the water storage housing, a second coupling structure disposed on a bottom portion of the sidewall structure, wherein the first coupling structure is configured to be removably coupled to the second coupling structure to thereby create a water-tight seal between the water storage housing and the base housing, and a translucent material disposed upon an upper opening of the water storage housing, wherein the translucent material is configured to receive the visible light from the plurality of LEDs and is configured to provide at least a portion of the visible light outwards in the radial direction.

According to another aspect of the invention, a water monitoring and treatment module is disclosed. The system may include a case with an opening, and a lid that fits tightly into the opening of the case, where when water is filled into the case and when the lid fits on the case, water does not leak away from the case. In some embodiments, the interior the case is coated with material that reacts with UV via a photo catalytic process, such as TiO2 (e.g. P-25 by Degussa, PC 500 by Millennium, or any other material comprising Anatase and/or Rutile). In various embodiments, the catalyst may be in the form of a nanoparticle, thin film, microsphere, or the like. The case has may include a region, e.g. on the side, on the top, on the bottom, where a UV fluorescent material is provided. In operation, that UV fluorescent material glows or emits light in the visible spectrum when the water is under UV irradiation. In some embodiments, other types of indicators may be used when the water is exposed to UV light. In various embodiments, the case includes an interior opening a at the bottom, where UV irradiation is supplied by a plurality of UV LEDs located below the bottom of the water containing area; the UV LEDs are powered by a battery. The battery is typically coupled to UV LED driver electronics, a communication wireless module, and the like. In some embodiments, the interior of the case has a photodiode detector placed in the line of sight of the UV-LED irradiation direction to help determine water clarity, amount of water present, presence of UV irradiation, or the like. In some embodiments, the case also has an electronic display region on the exterior that indicates the presence of UV irradiation.

Various additional objects, features and advantages of the present invention can be more fully appreciated with reference to the detailed description and accompanying drawings that follow.

BRIEF DESCRIPTION OF THE DRAWINGS

In order to more fully understand the present invention, reference is made to the accompanying drawings. Understanding that these drawings are not to be considered limitations in the scope of the invention, the presently described embodiments and the presently understood best mode of the invention are described with additional detail through use of the accompanying drawings in which.

DETAILED DESCRIPTION

Figure 1:
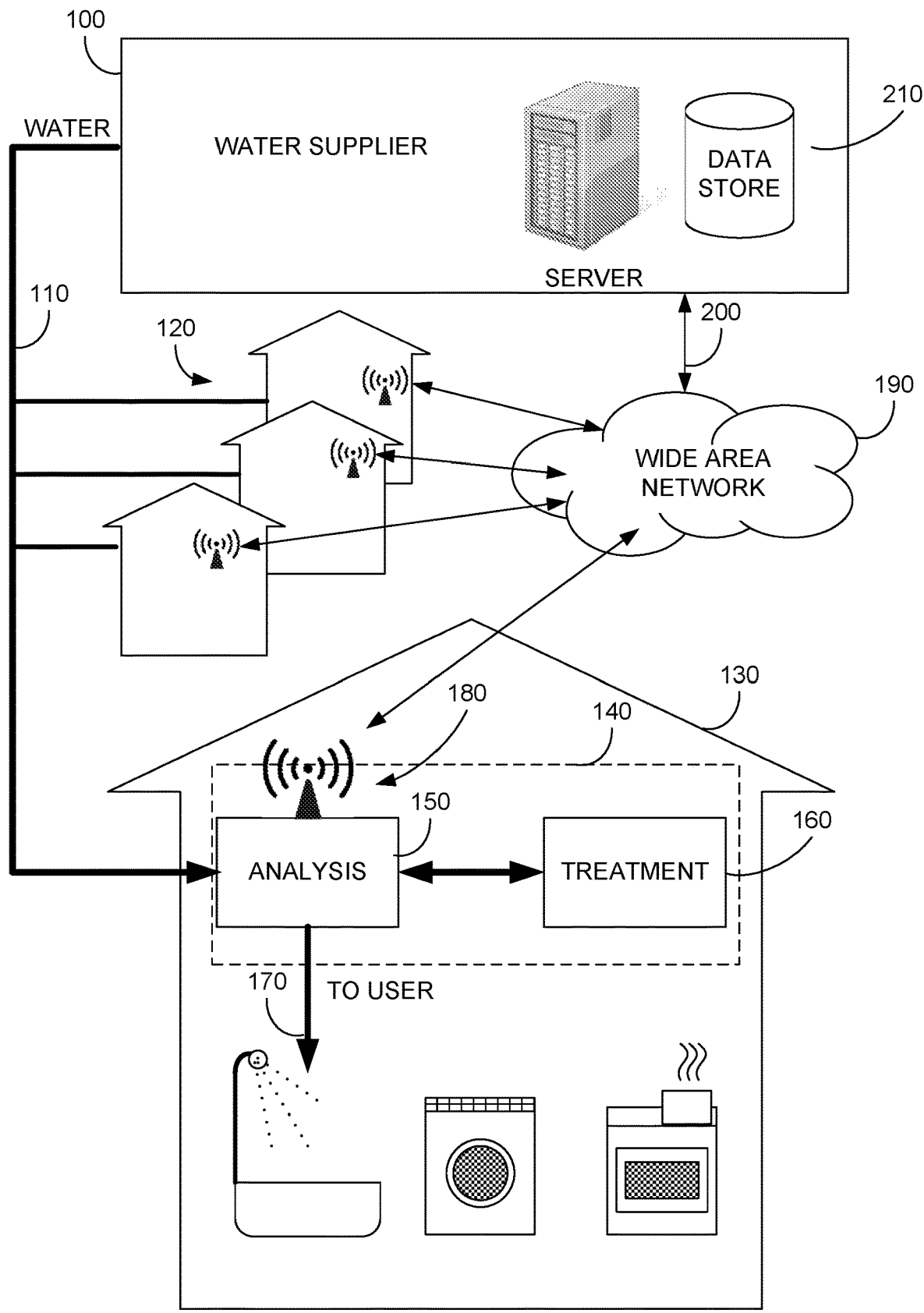
FIG. 1 illustrates a system diagram of various embodiments of the present invention.

FIG. 1 illustrates an embodiment of the present invention. More specifically, FIG. 1 illustrates a water supplier 100 supplying water 110 to water customers 120. Within a typical water customer 130, a device 140 is provided. In the present example, device 140 includes a water analysis device 150 and a water treatment device 160. As will be discussed further below, water analysis device 150 can perform an impurity analysis or optical transmittance, or optical absorbance analysis on incoming water 110, and water treatment device 160 can treat incoming water 110 and output treated water 170. Water analysis device 150 can also perform an impurity analysis or optical transmittance, or optical absorbance analysis on the treated water 170. If the treated water 170 is within predetermined impurity thresholds, it may be provided to the user, and in some embodiments, if the treated water exceeds the predetermined impurity thresholds, the treated water 170 will not be provided to the user.

In the embodiments illustrated in FIG. 1, water customers 120 each have a device 140 installed that performs the analysis and treatment functionality. As shown, each device 140 includes a wired or wireless communication portion 180 which can transmit data via a wide area network 190, back to water supplier 100. In various embodiments, the data may include an impurity analysis or optical transmittance, or optical absorbance analysis of the incoming water 110 and/or the treated water. As illustrated, the data 200 can be stored in a data store 210 associated with water supplier 100. In other embodiments, data store 210 may be associated with a third-party not associated with water supplier 100, such as a local water control agency, the EPA, a governmental body, a non-governmental organization, a commercial company, a non-profit organization, or the like.

Figure 2A:
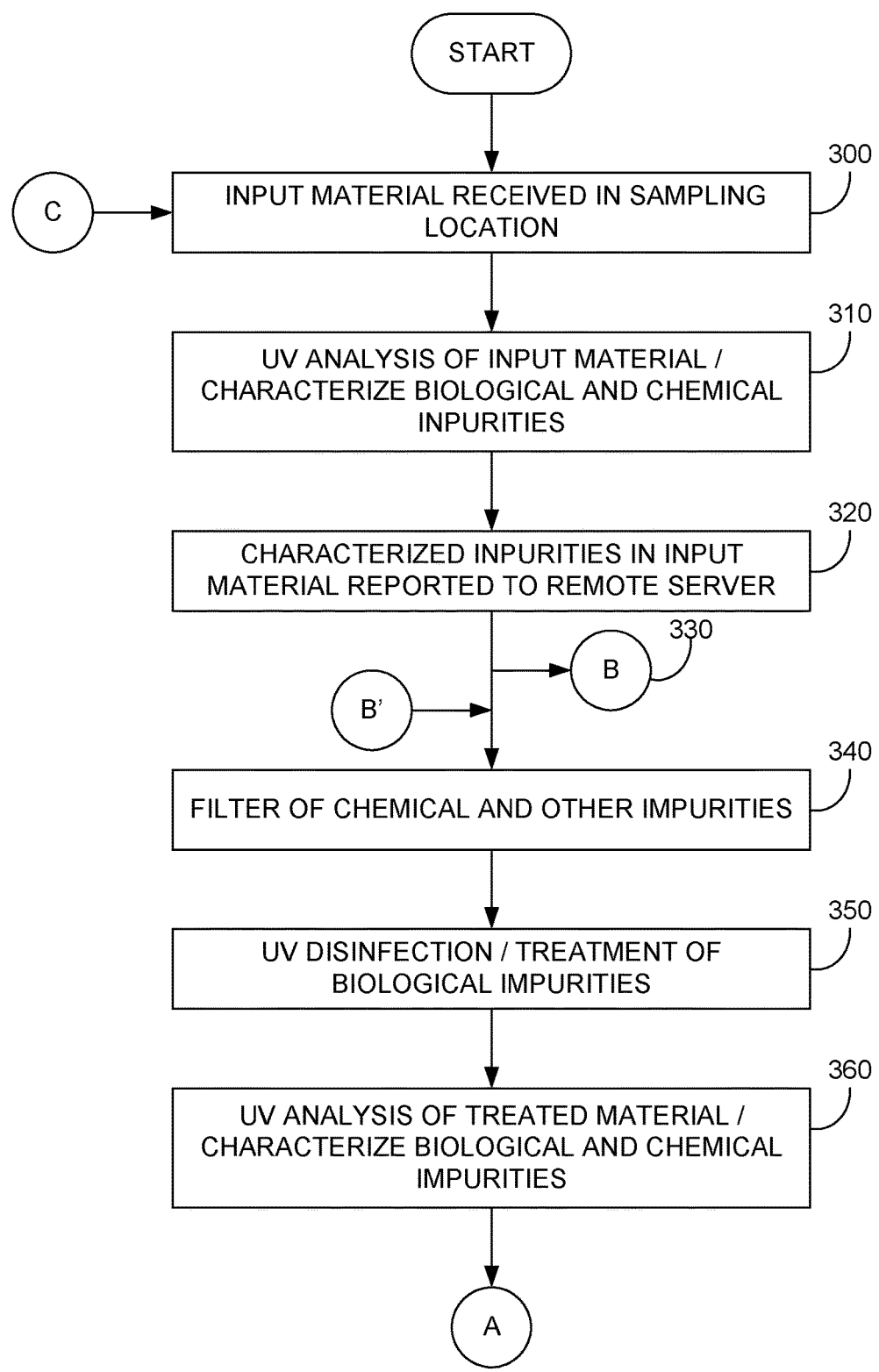
FIGS. 2A-B illustrate a block diagram of a flow chart according to some embodiments of the present invention.
Figure 2B:
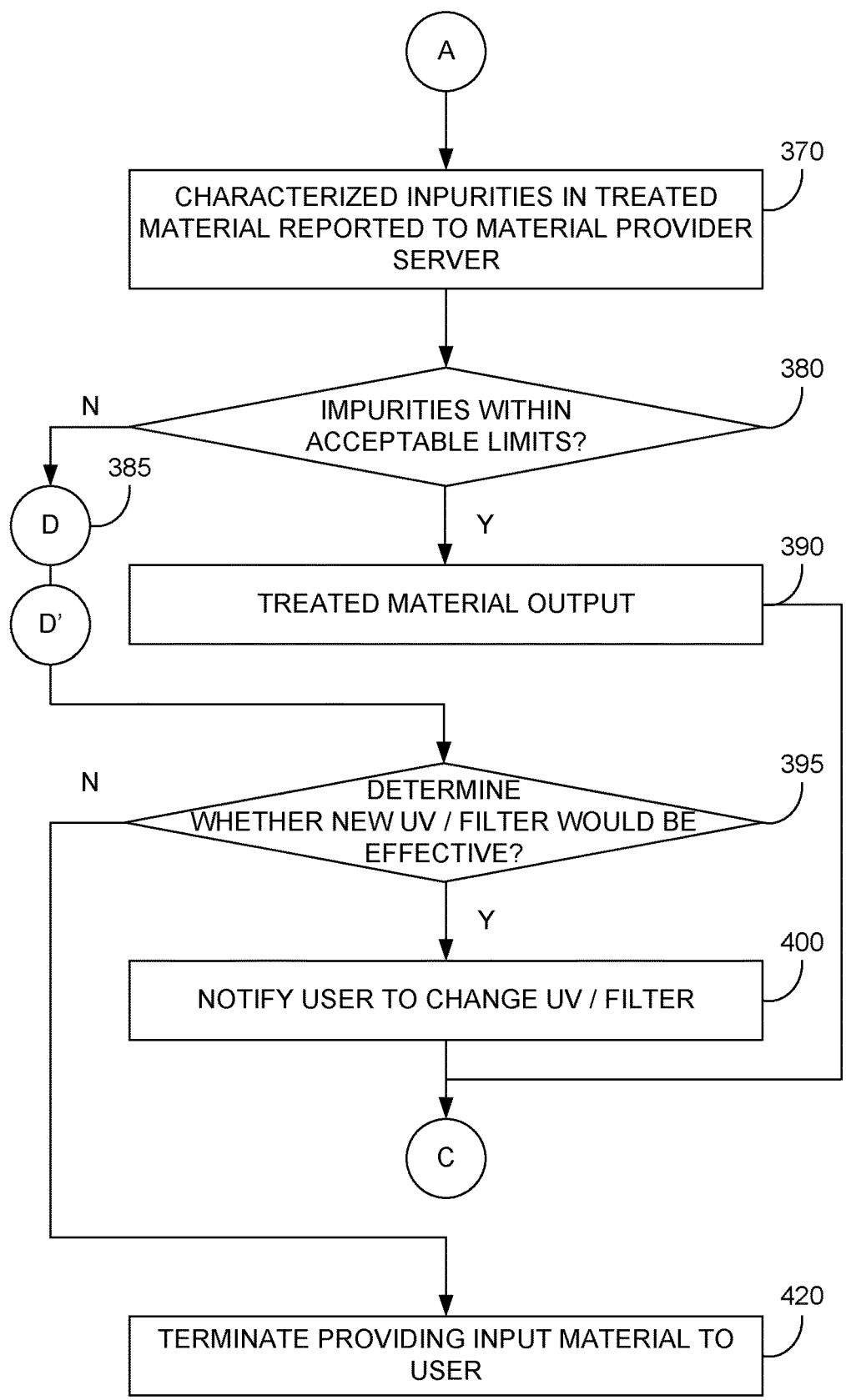

FIGS. 2A-B illustrate a flow diagram according to various embodiments of the present invention. More specifically, FIGS. 2A-B illustrate an example of a process performed at a typical water customer location, such as water customer 130, in FIG. 1. Initially water is provided to water customer 130, step 300. In other embodiments, water may be replaced with other fluids, such as gasoline, or other liquid, or beverage, and the customers may be companies, power plants, or the like.

In various embodiments, when device 140 receives the input water, an initial analysis can be performed, step 310 (optional). In various embodiments, one or more UV LEDs (with emission peak wavelength in the spectral range between 210 nm and 280 nm, or between 270 nm and 340 nm, or between 330 nm and 395 nm, or the like) may be used to illuminate the input water, and one or more optical sensors (such as, a photodiode, a photo detector, a spectrometer, or the like) may be used to detect responses to the UV illumination. In some embodiments, UV LEDs being developed by the assignee of the present invention may be used to illuminate the input water sample with UV light within a range of wavelengths from about 210 nm to about 365 nm, among other possible wavelengths, such as 385 nm. The UV LEDs may include some UV LEDs having a peak at about 280 nm, some UV LEDs having a peak at about 320 nm, or the like. By having multiple peaks of UV wavelengths, biological impurities having different response characteristics may be determined. For instance, different wavelength LEDs may be individually turned on by using a LED driver system that can pulse through a combination of UV LED wavelengths (frequency) peaked from 254 nm, 265 nm, 280 nm, 310 nm to 365 nm. For example, viruses may respond to a first UV LED characterized by a first UV frequency (e.g. fluoresce), bacteria may respond to a second UV LED characterized by a second UV frequency (e.g. fluoresce), and the like. In various embodiments, biological contaminants may include cryptosporidium, giardia, legionella, coliform, viruses, and the like.), or in another embodiment, contaminations can be suspended solids or particles in the water.

In response to the UV illumination, biological impurities may respond with characteristic responses. For example, pathogens that are exposed to first UV frequency light may reflect the UV frequency light, other impurities that are exposed to second UV frequency light may fluoresce, and the like. In some embodiments, the intensity of the responses as well as the wavelength are recorded.

In various embodiments, other types of testing may be performed upon the input water to determine chemical impurities (e.g. chlorine, lead, arsenic, organic compounds). For example, it is believed that methods for testing levels of lead, arsenic, and other harmful chemicals, are well-known, and can be used with embodiments of the present invention.

In various embodiments, the wavelengths of the responses to the UV illumination may be correlated to particular biological impurities, and the intensities may be correlated to the amount/percentage of the biological impurities. Further, based upon the chemical impurity analysis, the amount/percentage of the chemical impurities can be determined. The amount/percentage of the biological impurities and chemical impurities can then be sent back to the water provider, step 320, as illustrated in FIG. 1.

In some embodiments, step 310 may simply include using a UV light source to illuminate the water and a UV light detector to determining the turbidity or clarity of the water. In other embodiments, step 320 need not be performed, or may be performed at a later time.

Figure 3A:
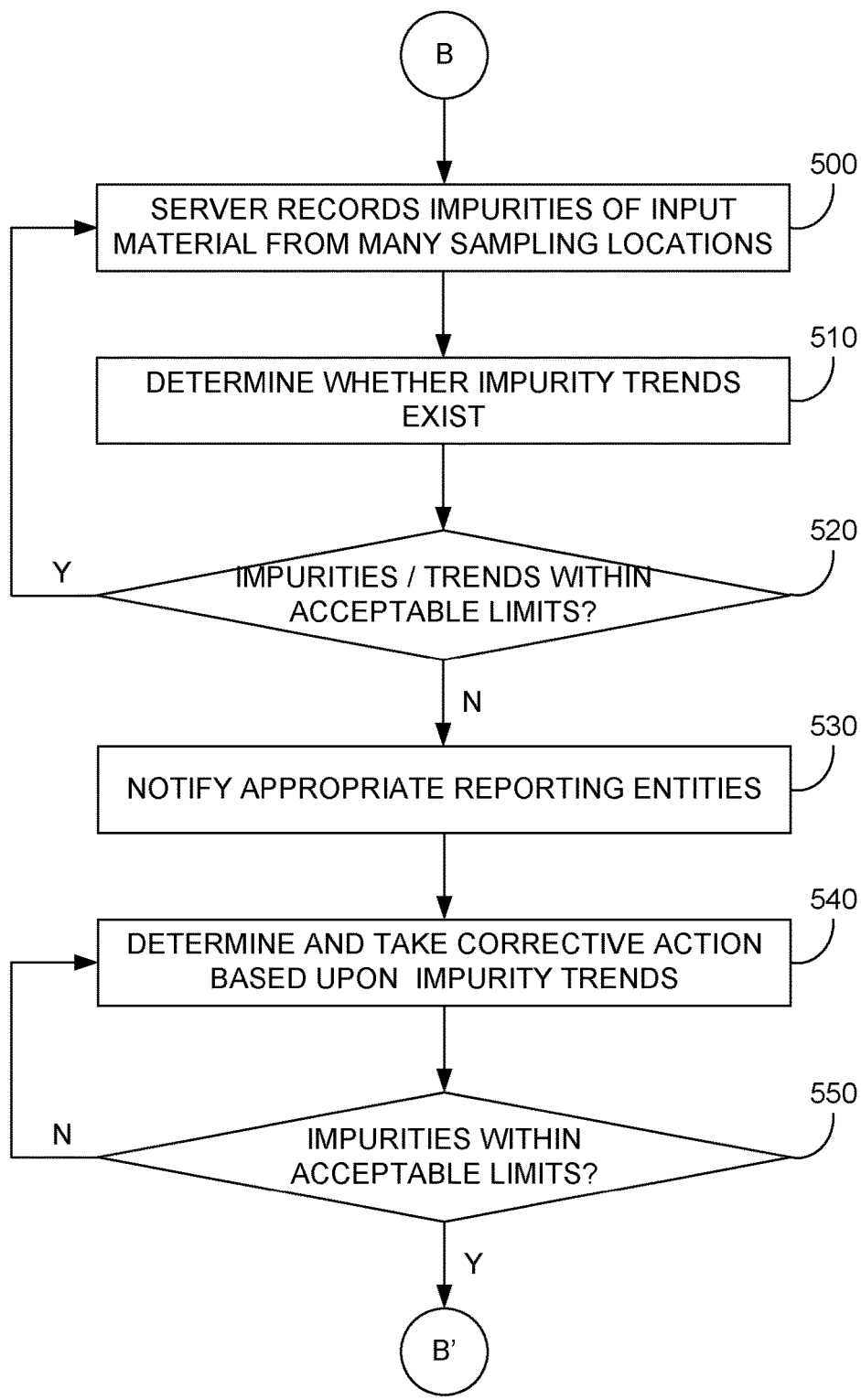
FIGS. 3A-B illustrate another block diagram of a flow chart according to some embodiments of the present invention.
Figure 3B:
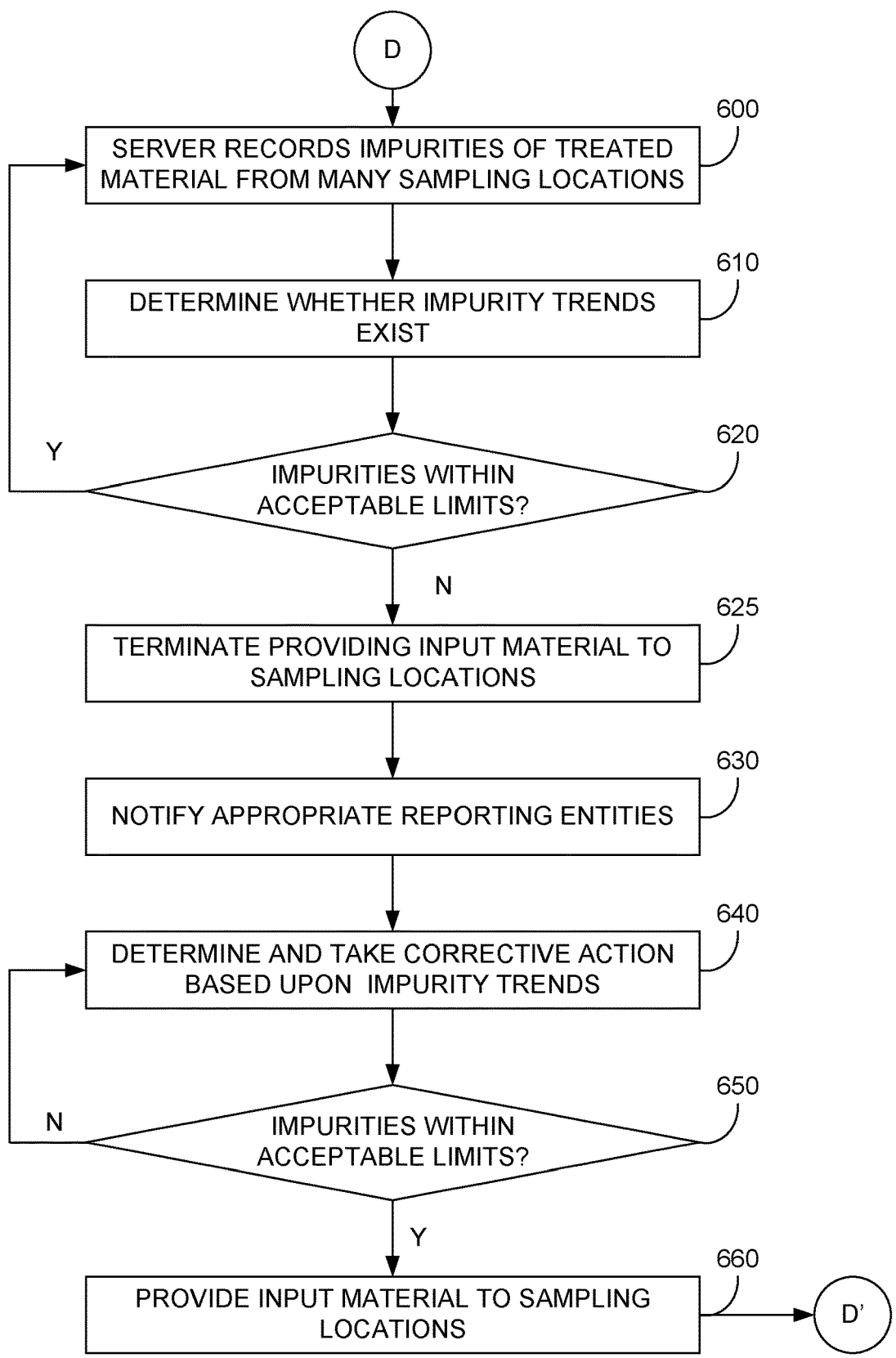

In FIG. 2A, after step 320, the processes illustrated in FIGS. 3A-B, steps 330, may be performed at the same time or at different times (asynchronously) from the remaining steps in FIGS. 2A-B.

Next, in various embodiments, a dedicated UV disinfection/treatment process may be performed, step 350 and a dedicated filtering process may be performed (e.g. filtering via an activated charcoal or carbon filter), step 340. In some embodiments, the UV disinfection or treatment process may also include UV LEDs currently under development by the present assignee. For example, UV LEDs having different UV frequency peaks, e.g. 220 nm, 240 nm, 260 nm, 320 nm, 340 nm, 365 nm, 375 nm, etc. may irradiate the input water. In some embodiments, the power output or intensity of the UV LEDs may be flat across the desired UV frequency range. In other embodiments, the power output of the UV LEDs may depend upon the type of biological contaminants that were determined in step 310, above. For example, if only viruses are determined, only UV LEDs having a peak of about 254 nm may be activated in step 350.

In some embodiments, in step 350 UV irradiation of the water, or liquid, may be performed in conjunction with a catalyst, such as TiO2, as mentioned above. TiO2 is selected as a catalyst because it is non-toxic, stable, has no smell, is not soluble in water, but reacts strongly with UV light. In such embodiments, UV illumination in the UV-A bans may irradiate an inner surface, or other element in the water that has a coating of TiO2. In response to the UV-A (from about 250 to about 400, especially around 340 nm) irradiation, the TiO2 will produce one or more water byproducts, such as reactive oxygen species. It is expected that many pathogens (e.g. viruses, bacteria, fungi, algae, cancer, *E. coli*, etc.) and harmful chemicals (e.g. antibiotics, artificial dies, pesticides, herbicides, pharmaceuticals, etc.) that are exposed to active oxygen species will be neutralized. In light of the above disclosure, other catalysts can be used and are considered within the scope of embodiments of the present invention.

In various embodiments, the dedicated filtering process of step 340 may be non-selective and not dependent upon the types of chemical impurities determined in step 310, above. For example, the filtering process may include activated charcoal to absorb any chlorine or organic compound in the input water.

In various embodiments, step 340 or a similar step may be performed prior to step 310. In such embodiments, for example, characterization (UV, white light, etc.) of the water is performed after filtering out certain contaminants, impurities, suspended particles, or the like. These particles may inhibit the use of UV light for decontamination purposes, accordingly, filtering out of particulates may be performed prior to characterization. In such embodiments, step 310 may determine whether the water can be treated by UV light, or whether the water is too cloudy. If the water is too cloudy, the UV disinfection/treatment in step 350 may not be effective. Accordingly, if the water is too cloudy, in step 380 etc., below, the water may be deemed unfit for disinfection, treatment and for consumption (or other use), step 420.

In various embodiments, the treated water can again be tested for biological and/or chemical impurities, step 360. This step may be performed with the same analysis module that performs step 310, above. In other embodiments, two analyses modules may be used, one for input water and one for treated water. Various embodiments allow water to flow relatively freely from the input water, through embodiments of the present invention, and to the treated water.

Next, the analysis data on the treated water may be sent to the remote server in step 370. In some embodiments, the analysis data of the input and treated water may be sent to the remote server together in this step. As mentioned previously, the remote server may take the analysis data and perform actions asynchronously from the steps described in FIGS. 2A-B. In some embodiments, the water analysis data maybe compared with data acquired at other user/customer locations globally, and feedback to the user/customer as indication of the local water quality.

In various embodiments, a processing module may review the analysis data of step 360 to determine whether one or more contaminants exceed a predetermined threshold for a contaminant, step 380. For example, based upon the UV analysis in step 360, it may be determined whether cryptosporidium is detected in the treated water. If not, the treated water may be allowed to flow to the user, step 390.

In various embodiments, if one or more contaminants are detected in the treated water, a notification is made to the water server, step 385, and a determination is made as to whether the UV disinfection or treatment of step 350 and filtering of step 340 should have remove the impurity, step 395. If so, a determination is made whether the UV disinfection/treatment module and/or the filtering module of steps 340 and 350 need to be replaced, step 400. If so, in step 410, the user may be directed to replace one or more of these modules, e.g. replace the activated charcoal filtering mechanism, or the like.

In some embodiments, a determination is made that the treated water is not able to be treated effectively, the water flow may be stopped, step 420. In other embodiments, the treated water may continue to flow to the user, but the user may be made aware that the treated water is not safe to drink directly out the tap. In some embodiments, one or more indicator lights may be illuminated to provide the signal to the user. In other embodiments, one or more text messages may automatically be sent to the user when the water contains unacceptable levels of impurities.

FIG. 3A-B illustrates various embodiments of the present invention. More specifically, the processes may be performed by a server associated material (e.g. water) supplier, a regulation agency, or other third party organization.

As was illustrated in FIG. 1, it is contemplated that multiple users have embodiments of the present invention, and these multiple perform analyses upon the incoming water (e.g. step 320, FIG. 2A), and report the results to the server in step 330, FIG. 2A. In FIG. 3A, the analyses upon the input water is received by the centralized server, step 500.

In various embodiments, the centralized server may determine whether there are any positive or negative contamination trends in the water received by users, step 510. In some embodiments, this may also be determined based upon currently received data, historical data, and/or other data previously gathered by the centralized server. In various embodiments, if the impurities/trends do not exceed certain limits, step 520, the process may return to monitoring incoming samples.

In various embodiments, when provided water exceeds the standards, notification may be sent to the water supplier management, governmental authorities, other monitoring group, water consumers, step 530. The notification may be via e-mail, text, text message, phone call, or the like. As an example, if a factory discharges a hazardous chemical into a water supply, when embodiments of the present invention located at a user's home detect the hazardous chemical, using the steps described above, Governmental authorities or the water supplier may activate an emergency notification system to automatically alert water customers that they should not use the water.

In response to determining there is a problem with the water provided to consumers, one or more corrective actions may be taken by the water supplier, step 540, until the water returns to an acceptable water quality, step 550. Many conventional methods for treat the water, prior to providing to the user, are contemplated, for example, adding additional chemicals (e.g. chlorine); shifting sources of water (e.g. from lake to well water); locating and reducing of sources of contamination (e.g. factories, agricultural run-off, sewage); and the like. Such actions may be short-range actions and/or long range actions.

As was illustrated in FIG. 1, it is contemplated that multiple users have embodiments of the present invention, and these multiple perform analyses upon the treated water (e.g. steps 340-350, FIG. 2A), and report the results to the server in step 385, FIG. 2B. In FIG. 3B, the analyses upon the input water is received by the centralized server, step 500.

In various embodiments, similar to the steps in FIG. 3A, the centralized server may determine whether there are any positive or negative contamination trends in the water received by users, step 610. In some embodiments, this may also be determined based upon currently received data, historical data, and/or other data previously gathered by the centralized server. In various embodiments, if the impurities/trends do not exceed certain limits, step 620, the process may return to monitoring incoming samples.

In various embodiments, when provided water exceeds the standards, the water supply may be automatically shut-off to one or more water customers, step 625. Additionally, notification may be sent to the water supplier management, governmental authorities, other monitoring group, water consumers, step 630. Again, the notification may be via e-mail, text, text message, phone call, or the like. As an example, if a factory discharges a hazardous chemical into a water supply, when embodiments of the present invention located at a user's home detect the hazardous chemical, within the treated water, Governmental authorities or the water supplier may activate an emergency notification system to automatically alert water customers that they should not use the water. In contrast to the process described in FIG. 3A, the focus within FIG. 3B is water that cannot be effectively treated by embodiments of the present invention.

In response to determining there is a problem with the water provided to consumers, one or more corrective actions may be taken by the water supplier, step 640, until the water returns to an acceptable water quality, step 650. In the short range, this may include replacing the water purification portions of embodiments of the present invention, at each water customer site. For example, replacing activated carbon filters, replacing particulate filters, adding additional UV light sources, and the like, step 660. Many conventional methods for treat the water, prior to providing to the user, are also contemplated, for example, adding additional chemicals (e.g. chlorine); shifting sources of water (e.g. from lake to well water); locating and reducing of sources of contamination (e.g. factories, agricultural run-off, sewage); and the like.

In various embodiments, device 140 in FIG. 1 may be embodied as a water treatment device such as a water filter in a garage or under the sink, a table top device, a water pitcher, a water bottle (e.g. sports bottle) or the like. As an example, a water pitcher or water bottle may be based upon the design described in U.S. Pat. No. 8,816,300 issued Aug. 26, 2014 and assigned to the present assignee.

Figure 4:
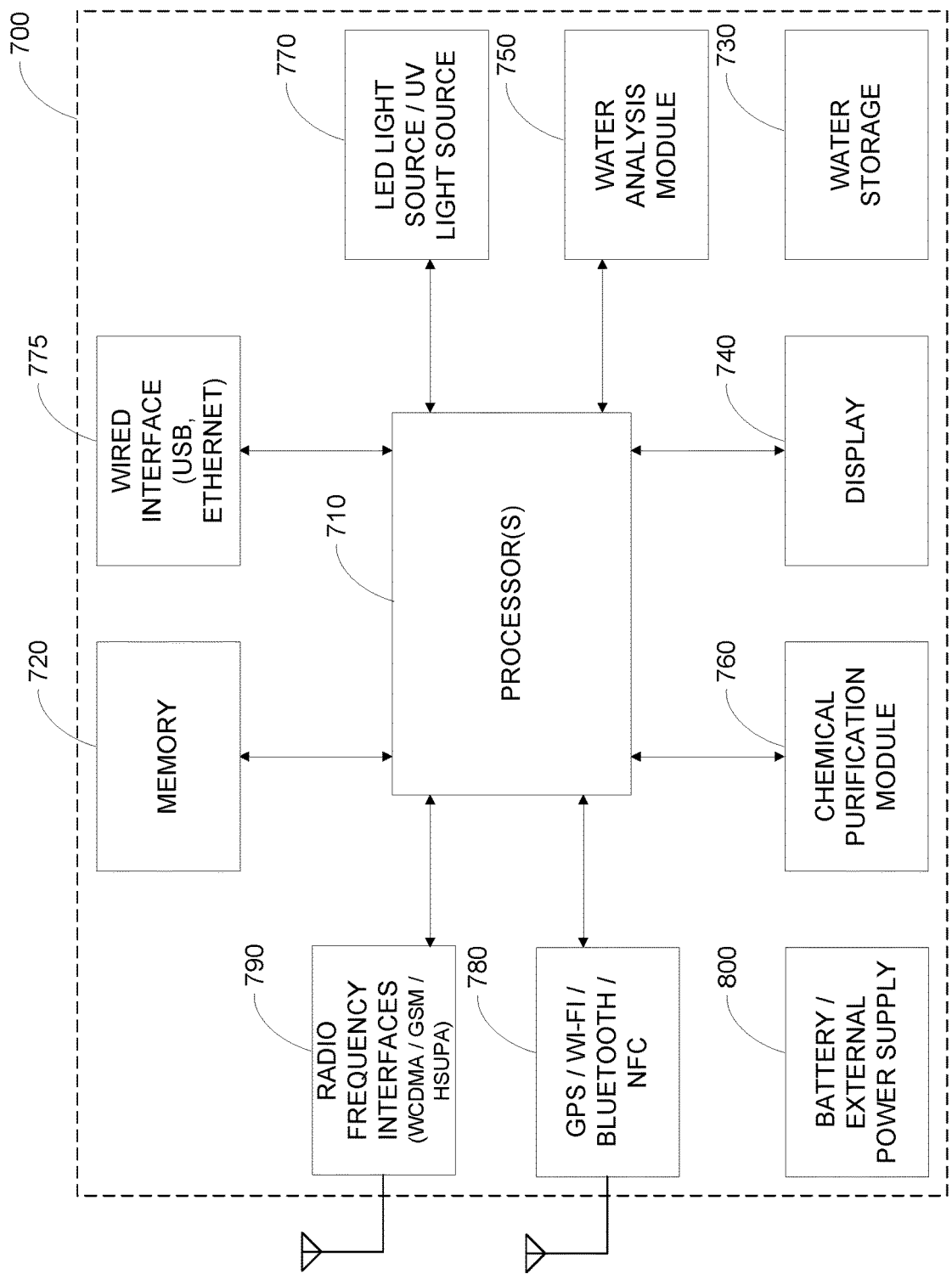
FIG. 4 illustrates a block diagram of portions of various embodiments of the present invention.

FIG. 4 illustrates a functional block diagram of various embodiments of the present invention. In FIG. 4, a device 700 typically includes an applications processor 710, memory 720, a display or other visual indicator 740, water analysis module 750, physical and chemical purification modules 760, UV purification modules 770, a treated water holding tank 730, and the like. Remote communications from and to device 700 can be provided by alternatively provided by a wired interface 775, a GPS/Wi-Fi/Bluetooth interface 780, RF interfaces 790, or the like. As illustrated, the above modules may communicate via an internal communication mechanism.

Typically, computing device 700 may include one or more processors 710. Such processors 710 may also be termed application processors, and may include a processor core, a video/graphics core, and other cores. Processors 710 may be a processor from Apple (51), Intel (Quark SE), NVidia (Tegra K1, X1), Marvell (Armada), Qualcomm (Snapdragon), Samsung, TI (OMAP), or the like. In various embodiments, the processor core may be an Intel processor, an ARM Holdings processor such as the Cortex-A, -M, -R or ARM series processors, or the like. Other processing capability may include audio processors, interface controllers, and the like. It is contemplated that other existing and/or later-developed processors may be used in various embodiments of the present invention, including processors having greater processing capability (e.g. Intel Core)

In various embodiments, memory 720 may include different types of memory (including memory controllers), such as flash memory (e.g. NOR, NAND), pseudo SRAM, DDR SDRAM, or the like. Memory 720 may be fixed within computing device 700 or removable (e.g. SD, SDHC, MMC, MINI SD, MICRO SD, CF, SIM). The above are examples of computer readable tangible media that may be used to store embodiments of the present invention, such as computer-executable software code (e.g. firmware, application programs), application data, operating system data or the like. It is contemplated that other existing and/or later-developed memory and memory technology may be used in various embodiments of the present invention.

In various embodiments, display 730 may be based upon a variety of current or later display technology including displays having touch-response, (e.g. resistive displays, capacitive displays, optical sensor displays, electromagnetic resonance, or the like). Any later-developed or conventional output display technology may be used for the output display, such as TFT-LCD, OLED, Plasma, trans-reflective (Pixel Qi), electronic ink (e.g. electrophoretic, electrowetting, interferometric modulating). In various embodiments, the resolution of such displays and the resolution of such touch sensors may be set based upon engineering or non-engineering factors (e.g. sales, marketing). In some embodiments of the present invention, a display output port, such as an HDMI-based port or DVI-based port may also be included.

In some embodiments of the present invention, water analysis module 750 may include multiple UV-LED light sources, each having unique UV light output frequencies, and one or more optical sensors. In various embodiment, UV-LED light sources have a relative narrow output peak (e.g. on the order of 20 nm), and are embodied as UV-LEDs currently being developed by the current assignee of the present application. The narrow output peaks allows embodiments of the present invention to differentiate between different types of contaminants and impurities. For example 210 nm to 250 nm range can detect Nitrites (NO2) and Nitrates (NO3), 250 nm to 380 nm can detect Total Organic Carbon (TOC), Dissolved Organic Carbon (DOC), Chemical Oxygen Demand (COD), Biochemical Oxygen Demand (BOD), Color (Hazen), Assimilable Organic Carbon (AOC, 240 nm and 300 nm range can detect Ozone, 360 to 395 nm can detect Benzene, Toluene and Xylene (BTX) and Turbidity (NTU) and the like. In some embodiments, a single water analysis module 750 may only analyze purified water, or may analyze incoming and purified water. In other embodiments, two water analysis modules 750 are provided, one for incoming water, and one for purified (treated) water.

In various embodiments, mechanical/chemical purification module 760 may include one or more porous membranes to filter-out contaminants particles suspended in the water. Additionally, module 760 may include any number of chemicals to reduce chemical contaminants in the water. In some examples, module 760 may include an activated charcoal filter to reduce chlorine and TOC (total organic carbon), DOC (dissolved organic carbon), COD (chemical oxygen demand), TOC, DOC and COD and the like. In various embodiments, incoming water is treated with module 760 prior to treatment with UV module 770.

In various embodiments, UV module 770 may be expose the water to different ranges of UV light to destroy different types of pathogens. For example, UV light in the 214 nm range is used to destroy MS2 coliphage, UV light in the 265 nm range is used to destroy *B. subtilis* and the like. In some embodiments, UV module 770 may also include embodiments of UV-LEDs under development by the current assignee. Such embodiments may directly target the pathogens determined in water analysis module 750 on the incoming water. For example, if only *B. subtilis* is detected in module 750, only UV-LEDs having an output range of about 260 nm to about 270 nm can be activated, to attack the *B. subtilis*. In other embodiments, a broad-band UV light source, e.g. medium pressure UV bulb may also be used, to purify the water, regardless of whether any pathogens are detected.

In some embodiments, a photo detector, such as a photodiode, or a PMT (photomultiplier), or a spectrometer, can be used in the system to monitor optical signal generated by the UV-LED when transmitted through the water.

In some embodiments, GPS receiving capability may also be included in various embodiments of the present invention, however is not required. The GPS functionality may provide the remote server with the geographic location of device 700. Any number of MEMS sensors, e.g. accelerometer, gyroscope, pressure sensors, or the like, may also be included to help estimate water consumption data. Some water consumption data may be based upon when and how long is the bottle or pitcher is tilted down into a water dispensing position, how much pressure is placed upon pressure sensors on the bottom of the water storage portion before and after consumption (indicating how much water is remaining and/or indicating how much UV-C light is required to sanitize the remaining water), and the like. In other embodiments, these sensors (e.g. accelerometers) can be used to help determine how long water has been sitting in the water storage, considering or ignoring UV sanitation. In further embodiments, other types of sensors may also be incorporated, such as humidity sensors, temperature sensors, user heart-beat sensors, and the like. In various embodiments, the above data or conclusions derived from the above data (e.g. how long has the water been sitting in the bottle) may be provided to a remote device, as discussed above.

FIG. 4 is representative of one computing device 700 capable of embodying the present invention. It will be readily apparent to one of ordinary skill in the art that many other hardware and software configurations are suitable for use with the present invention. Embodiments of the present invention may include at least some but need not include all of the functional blocks illustrated in FIG. 4. Further, it should be understood that multiple functional blocks may be embodied into a single physical package or device, and various functional blocks may be divided and be performed among separate physical packages or devices.

Further embodiments can be envisioned to one of ordinary skill in the art after reading this disclosure. For example, device 700 may be powered by any number of sources 800 including: AC from a wall outlet, solar-derived power, battery, manual crank or the like. As one example, a side wall of a portable water bottle may include solar cells, for on-the go charging.

Figure 5:
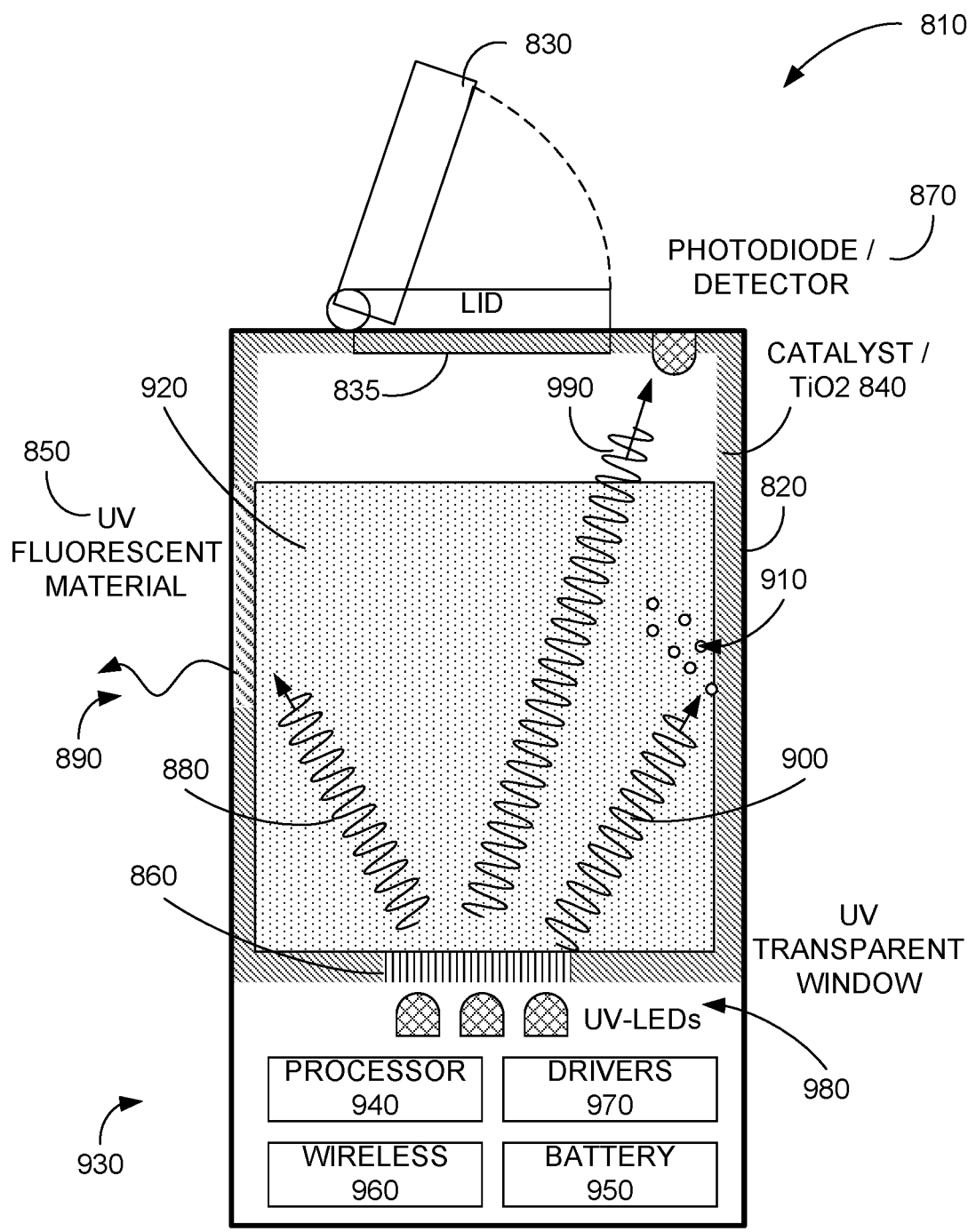
FIG. 5 illustrates cross-section of various embodiments of the present invention.

FIG. 5 illustrates an example of another embodiment of the present invention. In this example, a portable water bottle 810 is illustrated. Water bottle 810 includes an external housing having an opening 830, and an inner watertight housing 840. External housing may be a metal or metal alloy, glass, a translucent material, or other UV blocking material. In some embodiments, opening 830 may include a filter 835 (e.g. carbon, charcoal, etc.) for incoming water. In various examples, as mentioned above, inner housing 840 may include a coating of a catalyst, such as TiO2, or the like. In some embodiments, a UV reactive material is not used, and the inner wall may be formed from UV reflective material, e.g. stainless steel, aluminum, coated glass; or the like. The inner housing 840 may include a UV fluorescent material region 850, a UV transmissive region 860, an a photo detector 870. In various embodiments, electronic components are disposed in a bottom portion 930 of water bottle 810. As was discussed above, various components may be provided, such as a processor 940, a power supply 950, a wired or wireless communication interface 960, LED drivers 970, and one or more UV-LEDs 980. In various embodiments, UV-LEDs 980 may include UV-A and/or UV-B LEDs or the like.

In various embodiments, as illustrated, in response to UV illumination 880, UV fluorescent material 850 provides visible light 890, which can be seen by a user. In some embodiments, material 850 may be in the shape of a logo, pattern, special design, or the like. The design would appear to glow when UV illumination 880 was present. Additionally, in response to UV illumination 900, the catalyst on inner housing 840 generates reactive oxygen species 910 within the liquid (e.g. water) 920. Additionally, as illustrated, UV or white light illumination 990 passes through liquid 920 and strikes photo detector (photo diode or spectrometer) 870. In various embodiments discussed above, the intensity of light indicates the clarity or turbidity of liquid 920. In some embodiments, various types of optical properties may be measured, such as optical transmission, optical absorption, optical reflectance, and optical fluorescence, and the like. Depending upon the intensity of detected light, the time for the UV sanitizing process may be modified (e.g. increased or decreased); the intensity of the UV LEDs may be modified; the UV sanitizing process may be aborted; and the like.

In various embodiments, water bottle 810 may transmit the turbidity data, the UV sanitization parameters, and the like through wireless interface 960 to a remote destination. For example, the data may be sent to a third-party remote server; to a user's smart device or home computer; or the like.

In other embodiments, combinations or sub-combinations of the above disclosed invention can be advantageously made. For example, in FIG. 5, one or more UV wave guides may extend from the bottom surface of inner housing 840 into liquid 920. Such embodiments could increase the diffusion of UV light within inner housing 840. In another embodiment, the filter in the filtration process may include TiO2 material inside, where upon water will flow through the filter and be exposed to the surface of the TiO2 material (TiO2 nano particle, thin film, micro sphere, powder, etc.) UV light may be optionally delivered to the TiO2 material located inside the filter via light guiding technology, such as optical fiber or optical light guide blades. Such embodiments will increase the surface area of the TiO2 material exposed to the liquid, thus the oxidation capability will increase.

Figure 6A:
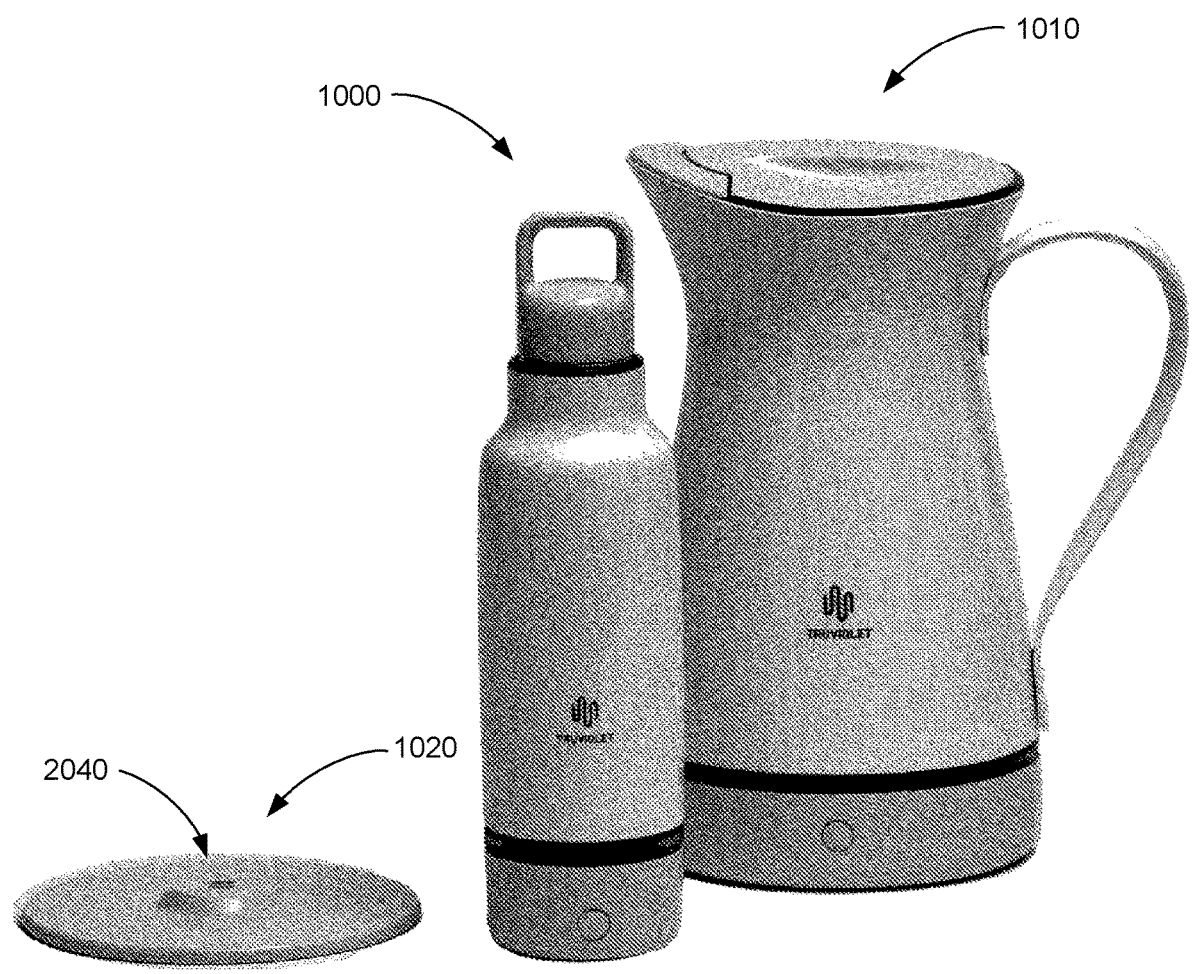
FIGS. 6A-C illustrate additional embodiments of the present invention.
Figure 6B:
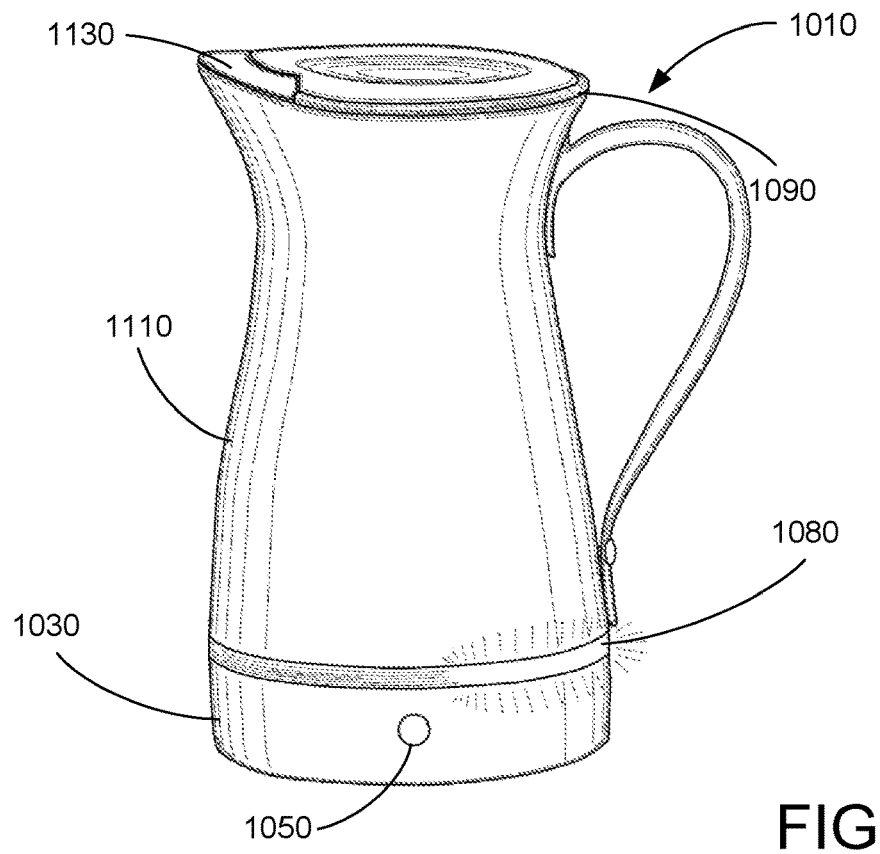
Figure 6C:
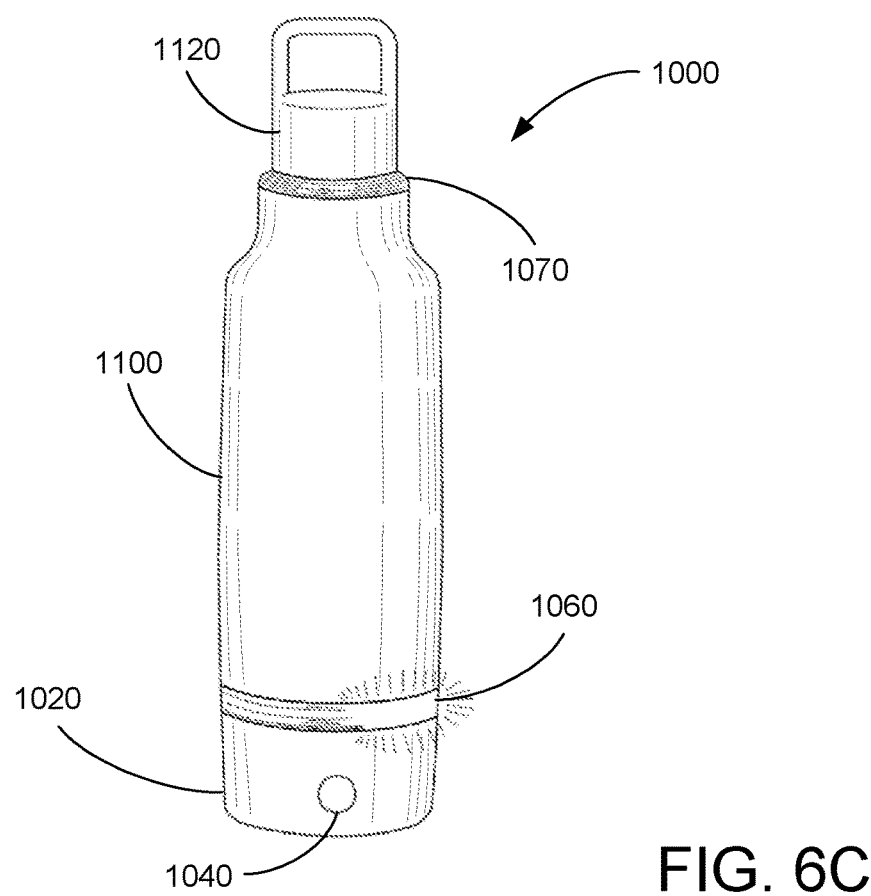

FIGS. 6A-C illustrate additional embodiments of the present invention. More specifically, FIG. 6A illustrates a water bottle 1000 embodiment, a water pitcher 1010 embodiment, as well as a charging dock 1020. In various embodiments, water bottle 1000 and water pitcher 1010 may include some or all of the features or functions illustrated in FIG. 5, above, and any other feature described herein.

In FIGS. 6B and 6C, water bottle 1000 and water pitcher 1010 each include a respective UV base portion 1020 and 1030, including respective activation (e.g. ON switch) buttons 1040 and 1050. Additionally, water bottle 1000 and water pitcher 1010 include a plurality of respective regions 1060 and 1070 and 1080 and 1090 that are visual indication regions, as will be described below. Further, respective side-wall sections 1100 and 1110 are illustrated, and respectively topped with a screw-on cap 1120 and a pitcher lid 1130.

In various embodiments, UV base portions 1020 and 1030 may include a charging interface, electronic circuitry, as well as LEDs, illustrated in FIG. 5. For example, in some embodiments, UV base portions 1020 and 1030 may include electronic circuitry such as a power supply, e.g. battery, a processor and memory; UV and visible light LEDs and drivers, buttons 1040 and 1050 (or switches, etc.). In other embodiments, wireless interfaces may be provided to communicate data from water bottle 1000 and water pitcher 1010 to a remote device (e.g. remote server, smart device, etc.). In other embodiments, water quality sensors may also be provided, for the purposes described above.

In the example illustrated in FIG. 6A, dock 1020 includes a portion 2040 that protrudes upward. Further, water bottle 1000 and water pitcher 1010 are physically configured to have an indent under the respective UV base portion 1020 and 1030 into which portion 2040 protrudes when water bottle 1000 or water pitcher 1010 are placed upon dock 1020. In some embodiments, portion 1140 may include electrodes that provide charging power to water bottle 1000 or water pitcher 1010; and in other embodiments, dock 1020 provides wireless charging functionality for water bottle 1000 and water pitcher 1010. In still other embodiments, dock 1020 may include a wired or wireless interface to enable water bottle 1000 and water pitcher 1010 to communicate to a remote device. In one example, usage data, etc. of water bottle 1000 or water pitcher 1010 from the last time these devices were docked to dock 1020 may be downloaded into dock 1020 when these devices are placed or docked thereto. This data may include number of UV sterilization cycles; an approximate amount of water consumed (e.g. based upon UV sterilization cycles, physical perturbations (as sensed by MEMS accelerometers or the like within UV base portions); time of day water is consumed; water quality data (described above); and the like. The data may then be uploaded to the remote device via dock 1020.

Figure 7A:
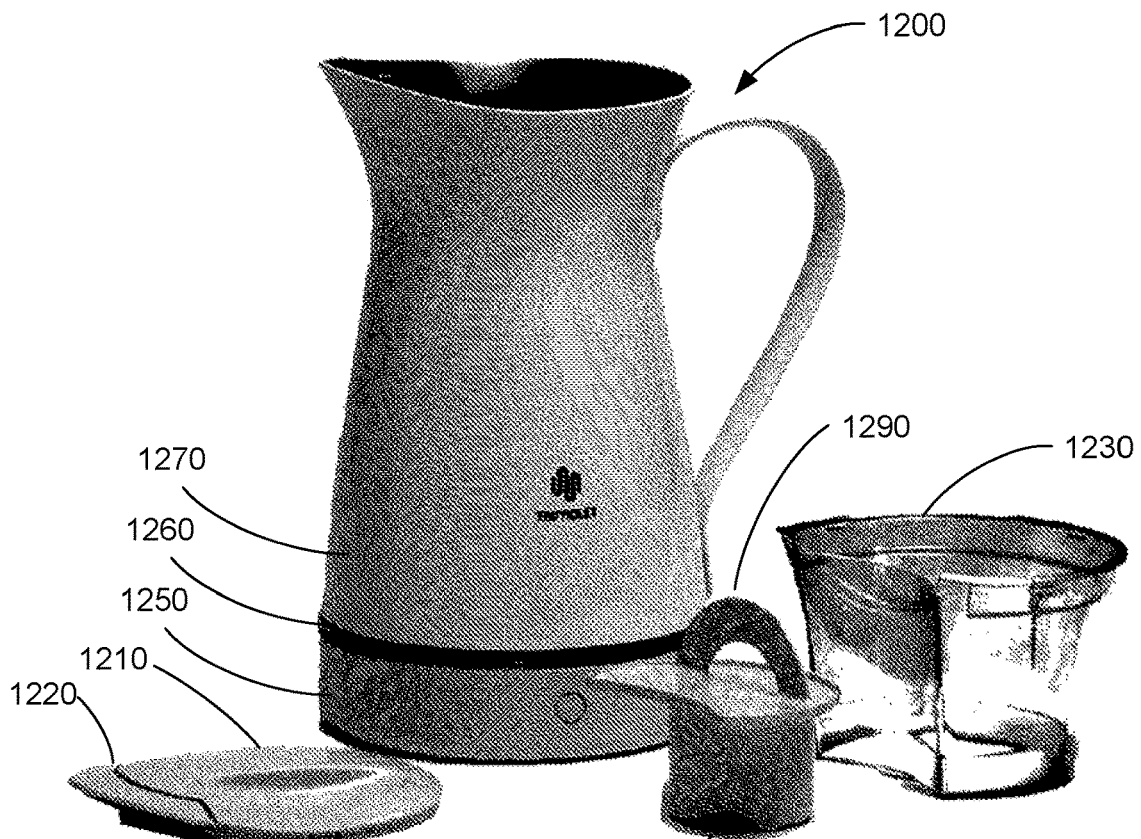
FIGS. 7A-B illustrate an example according to various embodiments of the present invention.
Figure 7B:
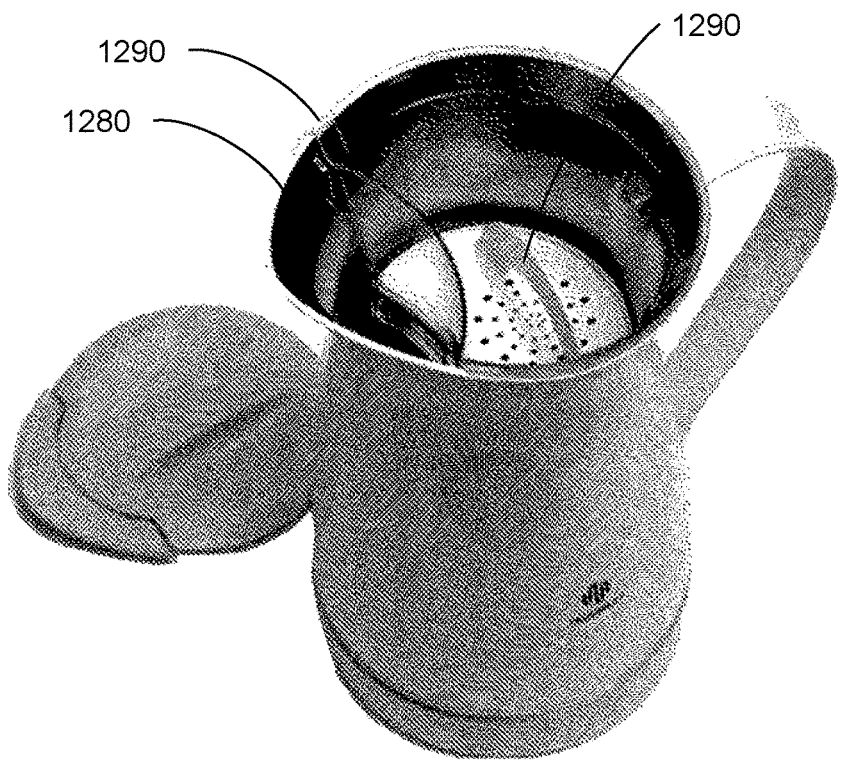

FIGS. 7A-B illustrates an example according to various embodiments of the present invention. More specifically, FIGS. 7A-B illustrate close-up views of a water pitcher 1200. In FIG. 7A, portions of water pitcher are illustrated and include a lid 1210 with a flap 1220, an incoming water portion 1230, a filter cartridge and filter cartridge holder 1240, a UV base portion 1250, a visual indicator portion 1260, and a storage portion 1270.

As illustrated in the example in FIG. 7B, filter cartridge and filter cartridge holder 1240 includes a handle 1290 and has a geometric shape that substantially matches a shape of incoming water portion 1230, such that holder 1240 can be disposed in the bottom of incoming water portion 1230. As illustrated in this example, the filter cartridge holder 1240 has a crescent-moon shape, although other shapes may also be used. In various embodiments, the filter cartridge and filter cartridge holder 140 may be manufactured from a UV transmissive material such that UV light within the water pitcher can prevent contaminants, biofilms, or the like from forming upon various surfaces of the filter cartridge or filter cartridge holder 140.

In various embodiments, incoming water portion 1230 also has a geometric shape that substantially matches a shape of the storage portion 1270, such that incoming water portion 1230 can sit approximately flush to a top lip 1280 of storage portion 1270. In various embodiments, incoming water portion 1230 includes a rounded over lip 1290 that is used to secure incoming water portion 1230 to lip 1280. In some embodiments, incoming water portion 1230 is formed of UV blocking material, e.g. Plexiglas, Lexan, or the like, and in other embodiments, incoming water portion 1230 allows some UV to be transmitted. In such embodiments, UV light within the water pitcher can prevent contaminants, biofilms, or the like from forming upon these surfaces, yet inhibit UV from reaching the user. Additionally, the material may be transparent, translucent or opaque to visible light in other embodiments. As will be discussed further below, in some embodiments, incoming water portion 1230 can receive visible light provided by UV base portion 1250, and direct the visible light outwards to the user, in a similar manner as visual indicator portion 1260.

In some embodiments, storage portion 1270 is detachable from UV base portion (typically including visual indicator portion 1260). In this example, when detached, storage portion 1270 may appears to a user to be a hollow tube that typically changes in shape and size in the vertical direction. In some embodiments, the interior of storage portion 1270 is formed from a UV reflective material such as stainless steel, aluminum, glass, Teflon, or the like. In some other embodiments, the interior of storage portion 1270 may be coated with a UV reactive material, such as TiO2, discussed above, to promote the formation of reactive ion species at the side-wall and to inhibit growth of contaminants.

As will be illustrated below, UV base portion 1250 is typically secured to storage portion 1270 by a series of screw-type threads on the outside of UV base portion 1250 and on the interior of storage portion 1270. Other mechanisms for attaching storage portion 1270 to UV base portion 1250 are contemplated, such as screw-type threads on the exterior of storage portion 1270 and in an interior of UV base portion 1250; via the use of rubber gaskets and compression fittings and or latches; or the like. In various embodiments, the seal between UV base portion 1250 and storage portion 1270 should be water-tight.

Figure 8:
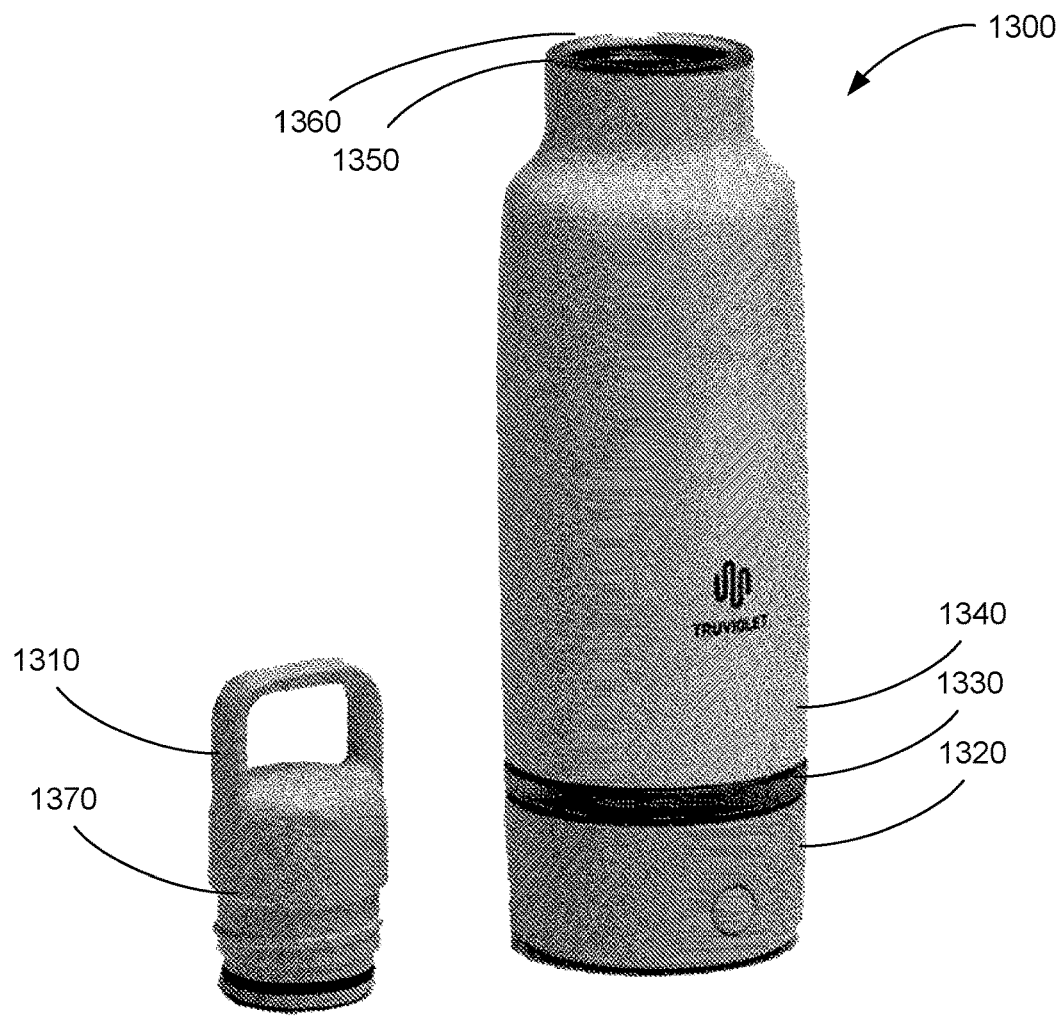
FIG. 8 illustrates an example according to various embodiments of the present invention.

FIG. 8 illustrates an example according to various embodiments of the present invention. More specifically, FIG. 8 illustrates close-up views of a water bottle 1300. In FIG. 8, portions of water bottle are illustrated and include a screw-in top 1310, a UV base portion 1320, a visual indicator portion 1330, and a storage portion 1340.

In some embodiments, storage portion 1340 is detachable from UV base portion 1320 (typically including visual indicator portion 1330). In this example, when detached, storage portion 1340 also appears to be a hollow tube that typically changes in shape and size in the vertical direction as shown. In some embodiments, the interior of storage portion 1340 is formed from a UV reflective material such as stainless steel, aluminum, glass, Teflon, or the like. In some other embodiments, the interior wall of storage portion 1340 may be coated with a UV reactive material, such as TiO2, discussed above. Storage portion 1340 typically includes an exterior wall also formed from material such as stainless steel, aluminum, plastic, or the like. Typically the exterior wall is separated from the interior wall by insulation, a vacuum, or the like.

As will be illustrated below, UV base portion 1320 is typically secured to storage portion 1340 by a series of screw-type threads on the outside of UV base portion 1320 and on the interior of storage portion 1340. Other mechanisms for attaching storage portion 1340 to UV base portion 1320 are also contemplated, as discussed above. In various embodiments, the seal between UV base portion 1320 and storage portion 1350 should also be water-tight. In light of the above, these mechanisms allow UV base portion 1320 to be separated from storage portion 1340 and allow UV base portion 1320 to be tightly coupled to storage portion 1340.

In some embodiments of the present invention, an upper lip portion 1350 of storage portion 1340 may include a ring of material 1360. In some embodiments, the ring of material 1360 is formed of UV blocking material, e.g. Plexiglas, Lexan, or the like. Additionally, the material may be transparent, translucent or opaque to visible light in other embodiments. As will be discussed further below, in some embodiments, ring of material 1360 can receive visible light provided by UV base portion 1320, and direct the visible light outwards to the user, in a similar manner as visual indicator portion 1330. In other embodiments, a ring of material 1370 may alternatively be disposed upon screw-in top 1310. As above, ring of material 1370 is typically formed of UV blocking material, e.g. Plexiglas, Lexan, or the like, while remaining transparent, translucent or opaque to visible light. Additionally, when screw-in top 1310 is secured to the upper lip portion 1350, ring of material 1370 may also receive visible light provided by UV base portion 1320, and direct the visible light outwards to the user, in a similar manner as visual indicator portion 1330.

In various embodiments, the design and cross-section shape of storage portion 1110 or storage portion 1100 may change versus height, i.e. it is not expected that storage portion 1270 or 1100 will be a perfect cylinder in some embodiments. As illustrated in the above figures, a specific design typically includes an approximately cylindrical base portion (or a truncated cone or an inverted truncated cone); a ring-shaped portion on top of the base portion that outputs illumination in different animated patterns (as will be illustrated below); and for a pitcher: a curved design for the storage portion having a smoothly formed spout; a handle attached to the storage portion; and a semi-circular or semi-ovoid-shape portion on top of the storage portion that also outputs illumination in different animated patterns; and for a bottle: an approximately cylindrical design that tapers near the top opening; a ring-shaped portion on the top opening that also outputs illumination in different animated patterns; and a bottle top having smoothly formed opening. In other embodiments only a sub-set of these design elements may be considered with the scope of the designs herein. For example, a water pitcher or a water bottle having an inverted truncated cone shape for a base portion (e.g. 1030, 1020) and a ring-shaped illumination portion (e.g. 1080, 1060) on top of the base portion that provides animated or static illumination may be considered with the scope of embodiments of designs of the present invention. As another example, a design may include those elements mentioned immediately above, including another illumination portion (e.g. 1090, 1070) of the top of the sidewalls that also provides animated or static illumination.

Figure 9:
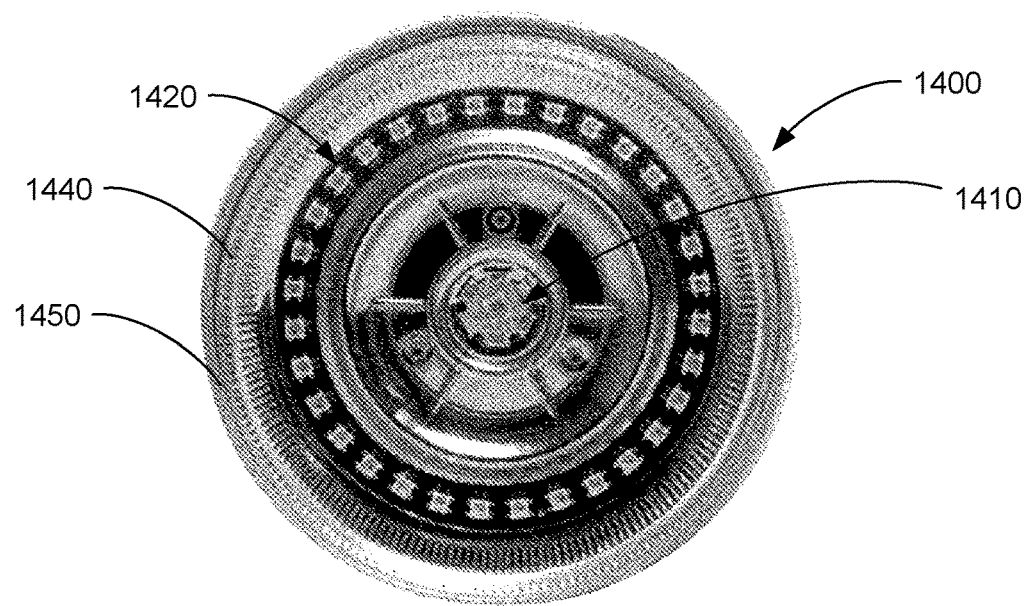
FIG. 9 illustrates an example according to various embodiments of the present invention.

FIG. 9 illustrates an example according to various embodiments of the present invention. More specifically, FIG. 9 illustrates a close-up views of a top view of a UV base portion 1400. In this example, UV base portion 1400 includes a UV-C light source 1410, multiple visible light sources 1420, a visual indicator portion 1440, and external threads 1450. In various embodiments of the present invention, UV-C light source 1410 includes UV-C LEDs mounted upon a substrate provided by the assignee of the present invention. In other embodiments, UV-C light source 1410 may have a different appearance, depending upon the specific manufacturer.

In various embodiments, visual indication portion 1440 may be formed from a UV blocking material, e.g. Plexiglas, Lexan, or the like. Additionally, visual indication portion 1440 may be transparent, translucent or opaque to visible light. In various embodiments, visual indication portion 1440 receives visible light from multiple visible light sources 1420 and directs the visible light radially outwards to the user. In this embodiment, visual indication portion 1440 includes external threads 1450 enabling UV base portion 1400 to be coupled to threads of a water storage portion, as discussed above.

In some embodiments of the present invention, UV-C light source 1410 and multiple visible light sources 1420, as well as other electronics and power supplies noted above, are electrically sealed within UV base portion 1400. A substantially UV transparent material, e.g. glass, quartz, sapphire, or the like may be used to protect the components from UV base portion 1400 from water sitting on UV base portion 1400. In another embodiments, a substantially UV transparent material is disposed primarily above UV-light source 1410, and cheaper material, e.g. Lexan is disposed over the other regions of UV base portion 1400, e.g. multiple visible light sources, etc. Buttons, power connections, and the like on UV base portion 1400 may also be protected from water via gaskets, rubberized or inductive switches, and the like. In some embodiments, instead of UV base portion 1400 having a transparent window, the water storage portions may have bottoms formed from substantially UV transparent material, e.g. glass, quartz, sapphire, or the like. The water storage portions thus resemble a cup or container. This transparent bottom then protects UV base portion 1400 from water damage. In still other embodiments, to further decrease potential water damage to UV base portion 1400, both UV base portion 1400 and water storage portions incorporate UV transparent material to protect water from UV base portion 1400.

In various examples, UV-C light source 1410 and visible light sources 1420 are illustrated disposed upon a material, such as stainless steel, aluminum, or the like, such that UV-C or visible light generated by these sources that is directed radially outwards is redirected generally upwards.

In various embodiments, multiple visible light sources 1420 are typically visible light LEDs and can be individually driven or addressed. In some examples, LEDs from light sources 1420 may have a similar wavelength or have different wavelengths of outputs (e.g. R, G, B). Accordingly, to a user, many different colors of light can be produced with different combinations of LED intensity. In some embodiments, the apparent color of light may be programmed by a user to help differentiate users' water bottles. For example, a mother's water bottle may be programmed to output a teal color, a daughter's water bottle may be programmed to output a pink color, a son's water bottle may be programmed to output a red color, and the like.

In some embodiments, an output color for multiple visible light sources 1420 serve as visual indicators to a user. For example, when a UV sanitization process is occurring, light sources 1420 may provide blue colored light; when water has not been sanitized, light sources 1420 may provide red colored light; when the water has been sanitized, light sources 1420 may provide green colored light; when the water bottle is almost empty, light sources 1420 may provide not output or brown colored light; and the like.

In various embodiments, multiple visible light sources 1420 are controlled commonly. As an example, when the water level within the water bottle is low, light sources 1420 may blink on and off at the same time; when the water has not been sanitized, light sources 1420 may blink on and off at the same time for a first number of times, and then stay on for a second period of time. The rate of blinking or alternation of on and off may provide the user with visual indications of status of the water bottle, or the like. As examples, during UV sanitation, the rate of blinking on and off of light sources 1420 may indicate how close to complete the process is, e.g. slower blinking rate at the beginning, faster blinking rate near the end, and solid on after completion; the rate of blinking or intensity of light sources 1420 may indicate the status of the power source within UV base portion 1400, e.g. a high duty cycle or rate of blinking when the battery is fully charged (e.g. appearance of a fast heart beat), a low duty cycle or rate of blinking rate when the battery is lower (e.g. appearance of a slower heart beat), and no light, when the battery is insufficient to perform a UV sterilization cycle (e.g. solid on or off).

In additional embodiments, multiple visible light sources 1420 may be controlled individually thus multiple patterns of blinking as well as intensity are enabled. As an example, when the water level within the water bottle is low, light sources 1420 may slowly turn on and off in succession around UV base portion 1400 (e.g. clock-wise or counter clock-wise); when the water has not been sanitized, every other light source from light sources 1420 may turn-on and off out of phase (e.g. odd light sources are turned on while even light sources are turned off, then even light sources are turned on while odd light sources are turned off); etc. The rate of blinking or alternation of on and off may also provide the user with visual indications of status of the water bottle. As examples, during UV sanitation, the rate of blinking on and off of light sources 1420 in succession may indicate how close to complete the process is, e.g. slower successive turning on and off rate of LEDs at the beginning, faster successive turning on and off rate of LEDs near the end, and solid on after completion; the rate of blinking or intensity of light sources 1420 may also indicate the status of the power source within UV base portion 1400, e.g. faster turning on and off of LEDs when the battery is fully charged, slower turning on and off of LEDs when the battery is lower, and no light or solid light, when the battery is insufficient to perform a UV sterilization cycle.

In still other embodiments, the number of LEDs in visible light sources 1420 indicates progress of a UV sanitation cycle. As an example, when a UV sanitation cycle is initiated, a few LEDs of light sources 1420 are turned on and remain on, as the UV sanitation continues, more and more LEDs of light sources 1420 are turned on and remain on, and as the UV sanitation completes, all of the LEDs of light sources 1420 are turned on and remain on. A user can thus readily see the progress of a UV sanitation cycle. Alternatively, all LEDs in visible light sources 1420 are initially turned on, and as UV sanitation progresses, particular LEDs are turned off, until no LEDs remain on (UV sanitation completed).

In light of the above disclosure, one of ordinary skill in the art will understand that many different combinations of the above visual feedback techniques are possible as well as other visual techniques not specifically discussed herein and are all contemplated in embodiments of the present invention.

Figure 10A:
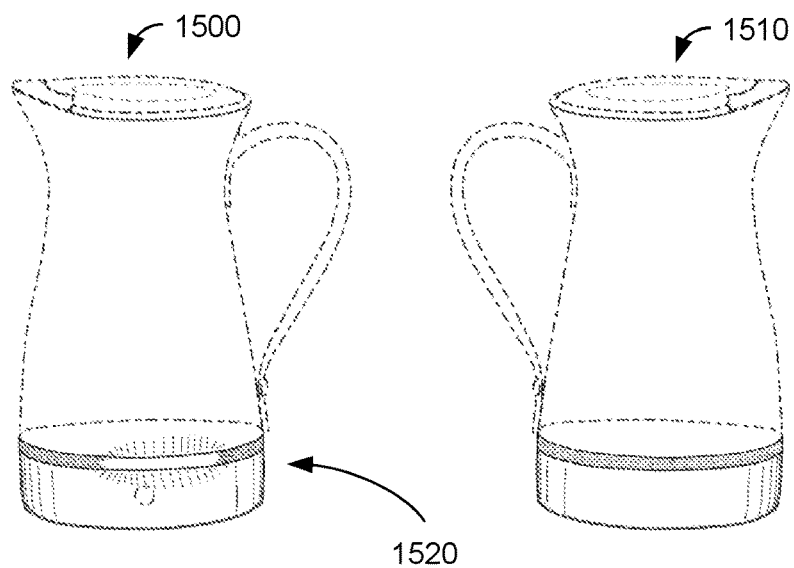
FIGS. 10A-H illustrate embodiments of the present invention.
Figure 10B:
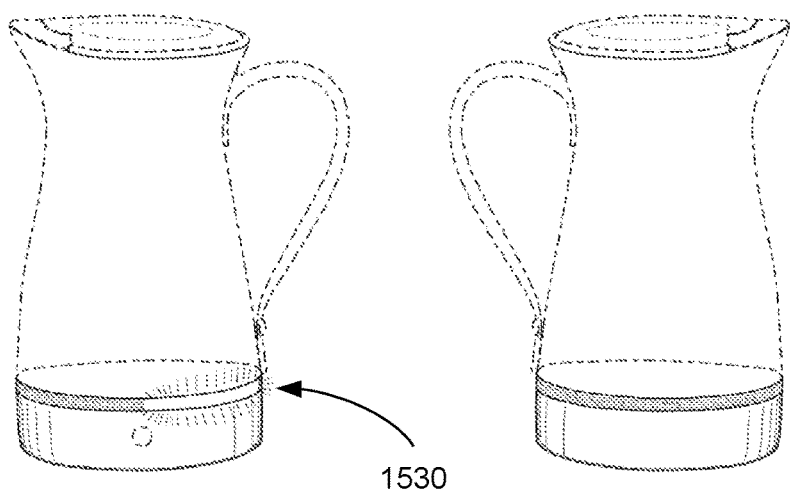
Figure 10C:
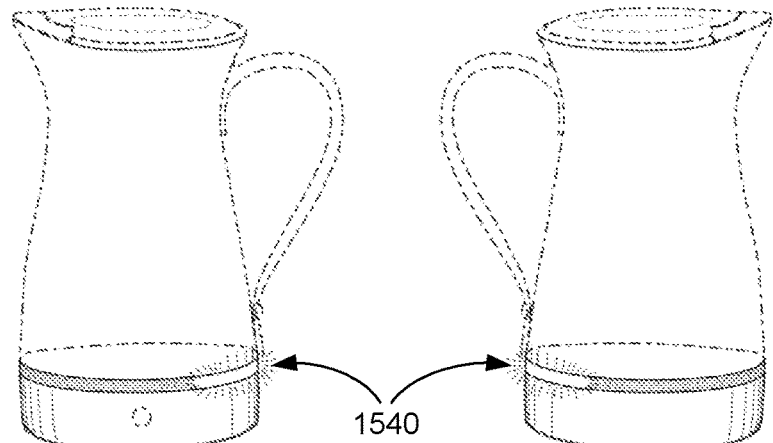
Figure 10D:
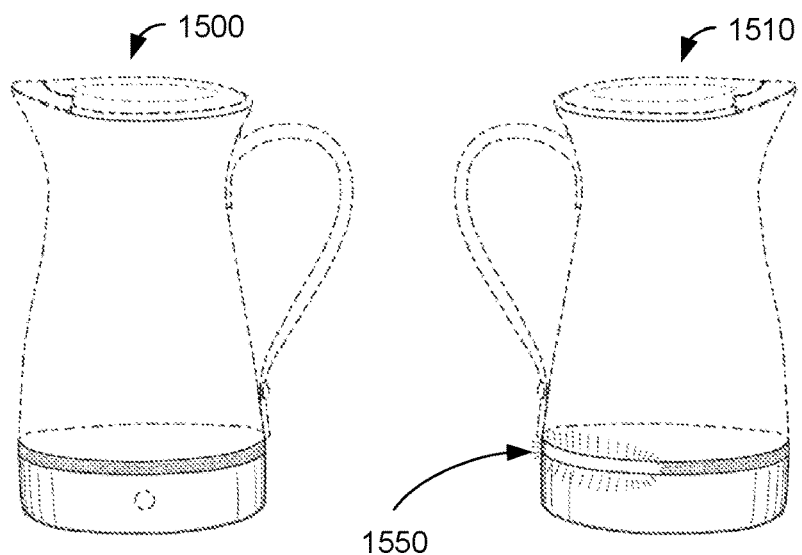
Figure 10E:
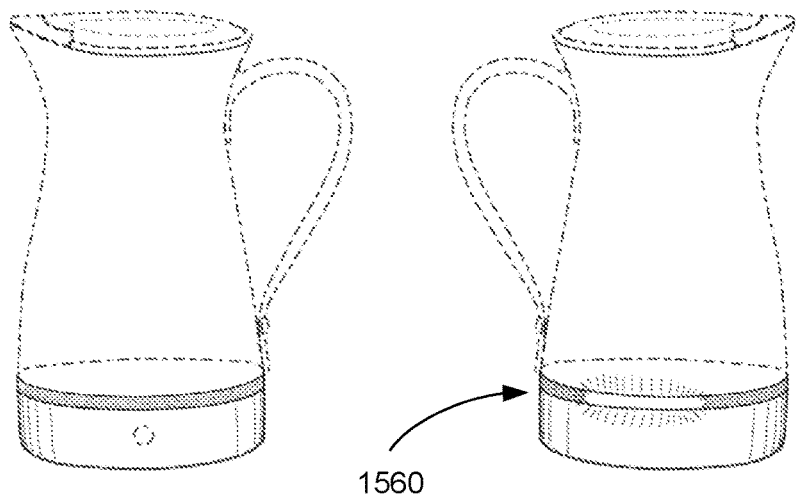
Figure 10F:
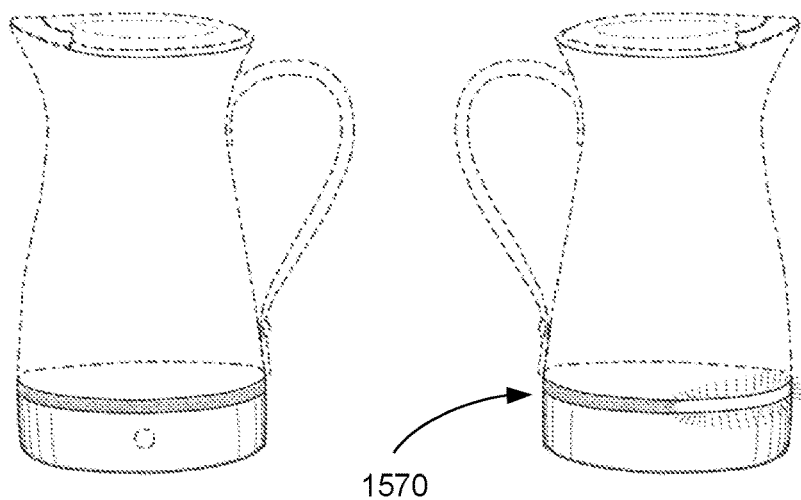
Figure 10G:
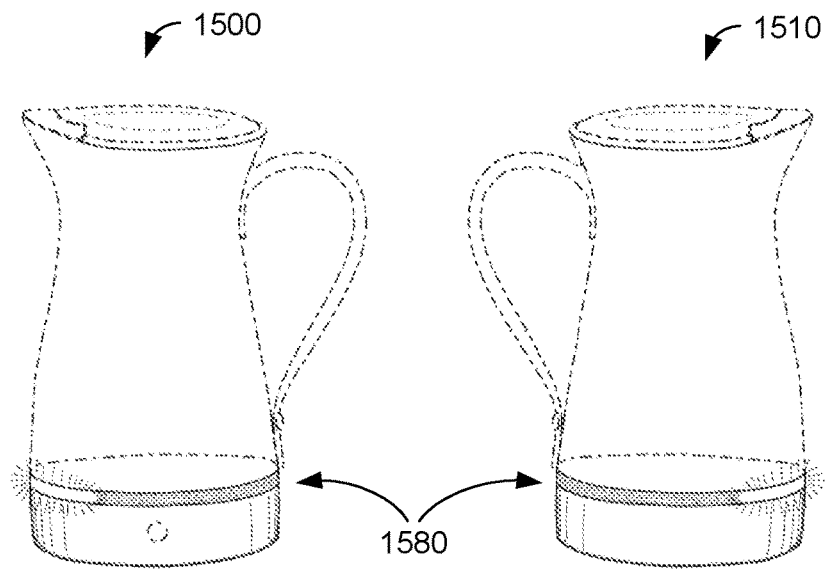
Figure 10H:
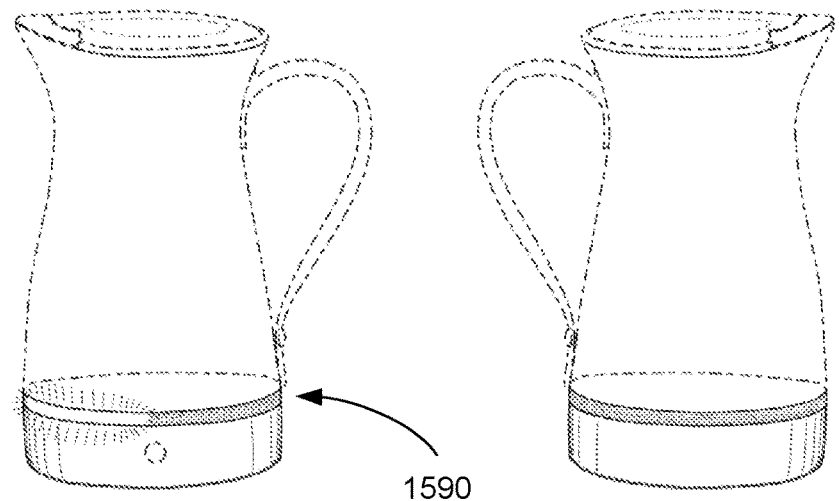

FIGS. 10A-H illustrate design embodiments of the present invention. More specifically, each of FIGS. 10A-H illustrate pairs of views (e.g. front views 1500 and rear views 1510) of a water storage device according to various embodiments of the present invention at the same time. FIGS. 10A-H illustrate the views with respect to time while performing an operation, e.g. a UV sanitizing cycle. In FIG. 10A. after initiation of the operation a first subset of LEDs 1520 are activated; in FIG. 10B, as time progresses, the first subset or a portion thereof is deactivated and a second subset of LEDs 1530 are activated. It should be understood that, LEDs may be part of multiple subsets, such as first subset 1520, second subset 1530, or the like; or LEDs may belong to only one subset. In FIG. 10C, a third subset of LEDs 1540 are then activated in progression, and continues to the rear side of the water storage device. As illustrated in FIGS. 10D-10F, additional subsets of LEDs 1550, 1560 and 1570 are activated on the rear sided of the water storage device, and various LEDs are deactivated, as shown. In FIG. 10G, a subsequent set of LEDs 1580 are then activated, and progresses back to the front side of the water storage device. Next, in FIG. 10H, LEDs 1590 are then activated on the front side of the water storage device. In various embodiments, the process of FIGS. 10A-10H may then be repeated; the process of FIGS. 10A-10H may be reversed; or the like. It should be understood that the inactivated LEDs may also appear to rotate about the base. Although illustrated as a water pitcher, embodiments of the present invention may be implemented as a water bottle, as illustrated in FIG. 6C. Additionally, in various design embodiments, an upper indicator region may also be provided that has the similar lighting patterns as described above.

Figure 11A:
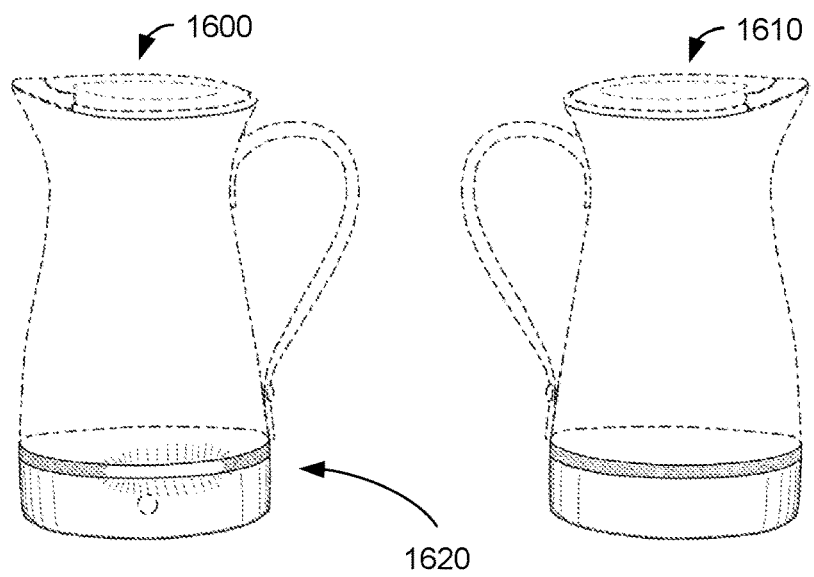
FIGS. 11A-H illustrate embodiments of the present invention.
Figure 11B:
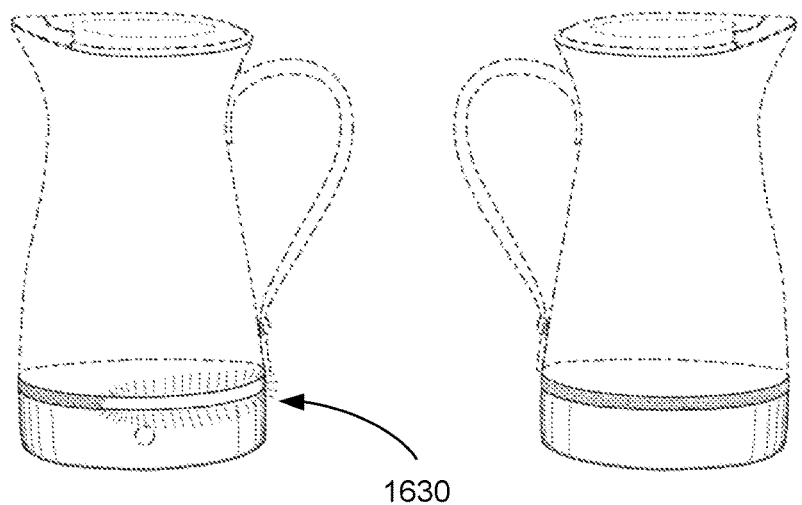
Figure 11C:
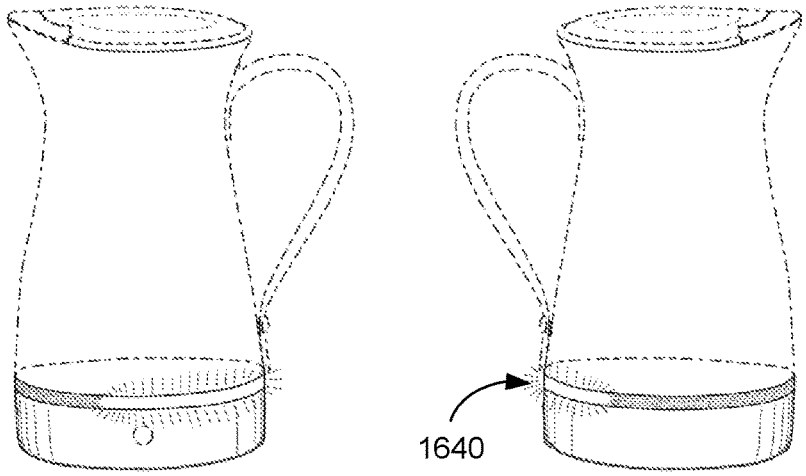
Figure 11D:
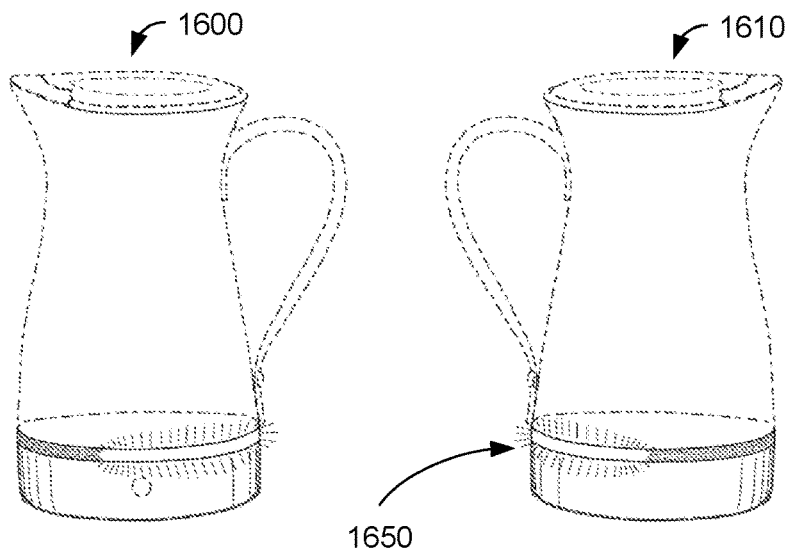
Figure 11E:
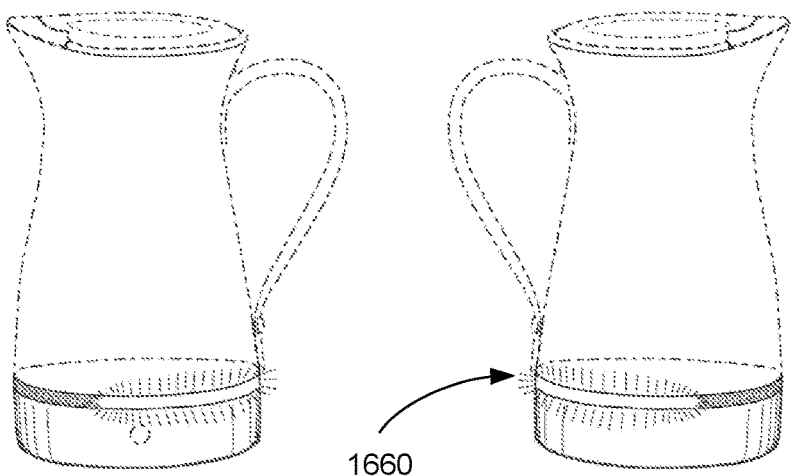
Figure 11F:
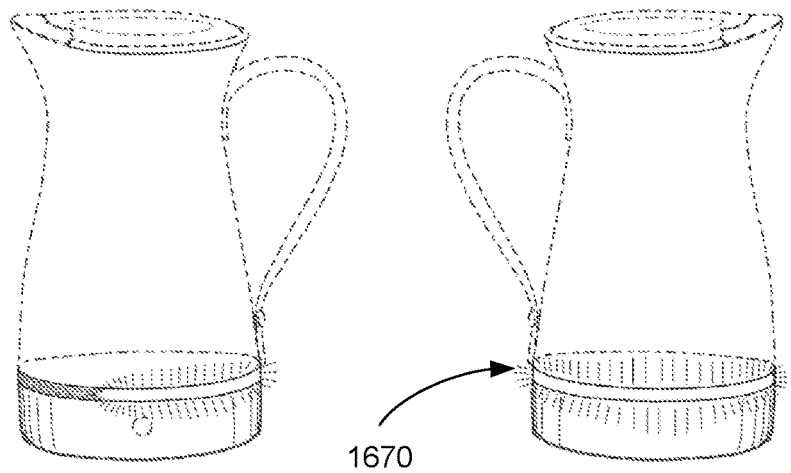
Figure 11G:
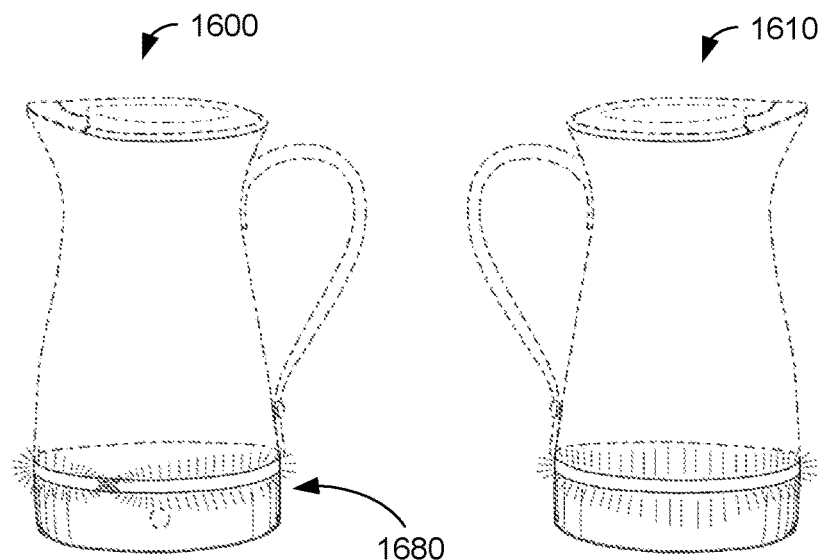
Figure 11H:
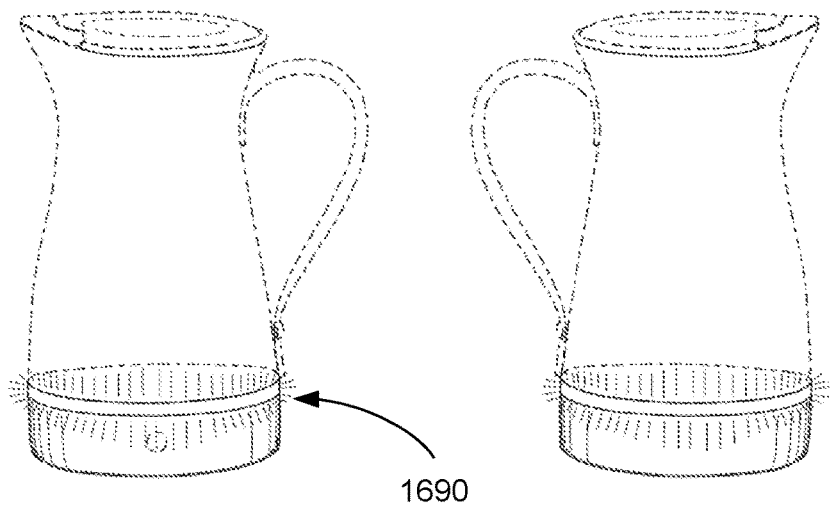

FIGS. 11A-H illustrate design embodiments of the present invention. More specifically, each of FIGS. 11A-H illustrate pairs of views (e.g. front views 1600 and rear views 1610) of a water storage device according to various embodiments of the present invention at the same time. FIGS. 11A-H illustrate the views with respect to time while performing an operation, e.g. a UV sanitizing cycle. In FIG. 11A. after initiation of the operation a first subset of LEDs 1620 are activated; in FIG. 11B, as time progresses, the first subset and a second subset of LEDs 1530 are activated. In FIG. 11C, a third subset of LEDs 1640 are then activated which continues to the rear side of the water storage device, while the first and second subset of LEDs remain activated. As illustrated in FIGS. 11D-11F, additional subsets of LEDs 1650, 1660 and 1670 are activated on the rear sided of the water storage device, while the previous LEDs remain activated, as shown. In FIG. 11G, a subsequent set of LEDs 1680 are then activated on the front side of the water storage device. Next, in FIG. 11H, LEDs 1690 are then activated on the front side of the water storage device. In various embodiments, the process of FIGS. 11A-11H may then be repeated; the process of FIGS. 11A-11H may be reversed; or the like. It should be understood that the inactivated LEDs may appear to shrink about the base. Although illustrated as a water pitcher, embodiments of the present invention may be implemented as a water bottle, as illustrated in FIG. 6C.

Additionally, in various design embodiments, an upper indicator region may also be provided that has the similar lighting patterns as described above.

As discussed above, the activation (and/or deactivation) of various of the LEDs may indicate many different operations, such as to indicate: that UV sanitation is occurring, the percentage progress of the UV sanitation process, the amount of battery life left, that communication with a remote server is occurring, the amount of time since the last sterilization process, and the like. Additionally, the color may also indicate various information such as: blue to indicate a sanitizing process is occurring, red for unsanitized water, green for sanitized water, brown for low power, and the like. Various combinations of activation/deactivation of lights in other types of patterns, and with various indicator colors is contemplated to be within the scope of embodiments of the present invention.

In various embodiments of the present invention, for example in the case of a UV sterilization bottle or a UV pitcher, as illustrated above, the UV sterilization cycle may be initiated upon a variety of conditions, such as: a user pushing a button on the device; the device automatically sensing when the bottle or pitcher are filled with water (e.g. a pressure sensor sensing an amount of water in the bottle or pitcher); automatically sensing when the lid or cap is removed (e.g. the user filling up with new water, the user drinking water and producing backwash, etc.); the processor determining that an amount of time has elapsed without the water being changed or sterilized (e.g. refreshing the water with another sterilization process (e.g. 2 minute sterilization) every 5 hours, etc.); the user initiating a sterilization process via pressing a button on a remote device (e.g. cell phone, smart device) and having the remote device communicate with the water pitcher or bottle; and the like.

In other embodiments of the present invention, additional design and functional features may be added. For example, the water storage portion of a water pitcher or water bottle may include a vertical slit running top to bottom and sealed with a plastic or glass insert. In such examples, the user may visually ascertain the amount of water stored with the pitcher and water bottle. A suitable design may appear as constant thickness or changing thickness stripe running down the side of the pitcher or water bottle, or the like.

Figure 12:
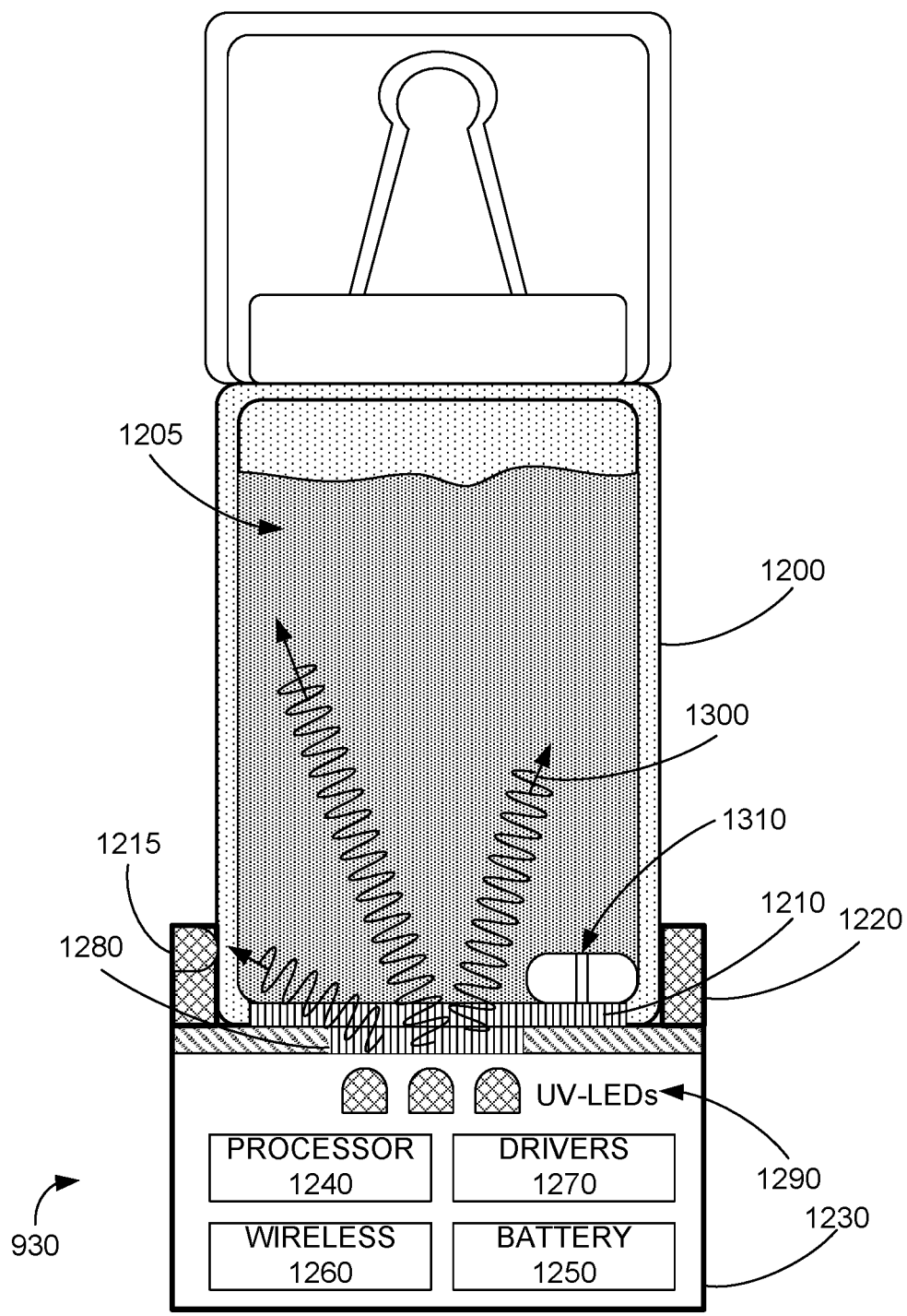
FIG. 12 illustrates an embodiment of the present invention.

FIG. 12 illustrates another embodiment of the present invention. More specifically, FIG. 12 illustrates a storage portion in the form of a bottle 1200, e.g. a baby bottle, a sports bottle, or the like, having a bottom formed of a UV transparent material 1210 that rests upon a cradle-like structure 1220 on a UV base portion 1230. Similar to the embodiment illustrated above and in FIG. 5, UV base portion 1230 includes the UV light source (UV LEDs) 1290 and optionally other functional blocks, such as a processor 1240, a power source 1250, a wireless communication portion 1260, and LED drivers 1270. In this embodiment, bottle 1200 can be set down upon UV base portion 1230 for sanitizing the liquid 1205 contents of bottle 1200 (e.g. milk, water, juice, sports drinks, etc.), and then separated from UV base portion 1230 for use (e.g. a baby or person drinking). In some embodiments, UV base portion 1230 may include a UV transparent material 1280 between bottle 1200 and UV light source 1290, although some embodiments may dispense with UV transparent material 1280.

Similar to embodiments described above, UV light 1300 may shine into bottle 1200 and sanitize or otherwise react with the liquid. UV light 1300 may illuminate the liquid upon demand or periodically. More specifically, UV light 1300 provided by UV base portion 1230 can be used to help facilitate sanitation (e.g. sanitize, periodically keep fresh) of the contents of bottle 1200, and/or UV light 1300 provided by UV base portion 1230 may modify (e.g. form reactive ion species, or the like) the contents of the bottle. For example, while bottle 1200 is cradled upon UV base portion 1230, every 30 minutes UV light 1300 may shine into bottle 1200 for a minute. This periodic illumination of the liquid with UV light 1300 maintains sanitation of the liquid, according to studies conducted by the inventors of the present invention. In various embodiments, UV light 1300 may be within the UV-C frequency range. Additionally or alternatively, in various embodiments, UV LED 1290 may include a UV-B LED, thus UV light 1300 may within the UV-B frequency range.

In other embodiments, additional features may be included. In one example, one or more pressure sensors may be provided into UV base portion 1230 so that the weight of bottle 1200 (e.g. baby bottle) before and after being used may be measure. The difference in weight may be used by processor 1240 to determine an approximate amount of liquid (e.g. water, juice, milk or the like) that is consumed. The consumption may then be recorded with respect to time and reported from UV base portion 1230 via wireless communication portion 1260 to a remote device (e.g. server, smart device, etc.), as was described above.

In some embodiments, UV light 1300 provided by UV base portion 1230 can be used to analyze various parameters (e.g. opacity) of the contents 1205 of the bottle (e.g. water, juice, milk, or the like). In some embodiments, a built-in opacity detector determines the opacity of the liquid present, e.g. milk, water, juice, etc. Based upon the opacity, the processor may increase or decrease a UV exposure time, increase or decrease a UV light intensity (e.g. 100%, 50%, etc.), or the like. For example, if the liquid 1205 is more opaque than water, UV light 1300 may have a higher intensity, a longer exposure time, a more frequent refresh schedule, and the like. In some embodiments, a detector 1215 similar to detector 870 illustrated in FIG. 5 may be used to determine opacity of the liquid. In FIG. 12, detector 1215 is illustrated on the side of bottle 1200, however the positioning of a UV-LED source and the positioning of the detector may vary according to engineering factors.

In some embodiments, to facilitate UV light 1300 exposure to liquids, especially liquids more opaque than water, a user may be instructed to periodically mechanically shake bottle 1200, e.g. in a stirring or a rotating motion, such that more of liquid 1205 stored therein can be exposed to UV light 1300. By ensuring that different portions of liquid 1205 are exposed to UV light 1300, liquid 1205 can be more thoroughly sanitized. In one example, UV base portion 1230 or a smart device may visually indicate to a user that bottle 1200 should be shaken or stirred via an LED light or text output screen. After the user does this mechanical agitation and replaces bottle 1200 onto UV base portion 1230, an additional UV light exposure cycle can be performed. After the sanitation cycle completes, the sanitation of liquid 1205, e.g. milk, is increased, and the milk can be consumed. In some embodiments, a mechanical agitator, 1310 may be incorporated into bottle 1200 and be controlled by UV base portion 1230. In one example, mechanical agitator 1310 may periodically stir liquid 1205 within bottle 1200 during a UV cycle so that the liquid may be uniformly exposed to UV light 1300. In another embodiment, an air bubbler mechanism may be used to agitate the liquid.

The inventors have performed various experiments to demonstrate the efficacy of agitation. In some tests, two chambers were used containing 10 liters of water and having a single UV LED at the tops. Next 0.1% Luria broth (LB) was added to the water to decrease the clarity of the water, e.g. to simulate a light absorbing liquid. This resulted in a measured penetration depth of the UV light in the sample to be 29% shorter than unfiltered tap water. The liquid in each chamber was then contaminated with E. coli bacteria to approximately 6.times.10 6 CFU/ml. After providing a series of UV light exposures to the liquid, samples were taken from multiple locations in the chambers after each exposure. In the case where no agitation was used during UV exposure, it took 12 minutes to reach 6 log 10 disinfection, and there was a large variation in disinfection efficacy across the chamber. In contrast, in the case where agitation was used during UV exposure, it took 6 minutes to reach 6 log 10 disinfection, and disinfection was uniform across the chamber.

Figure 13:
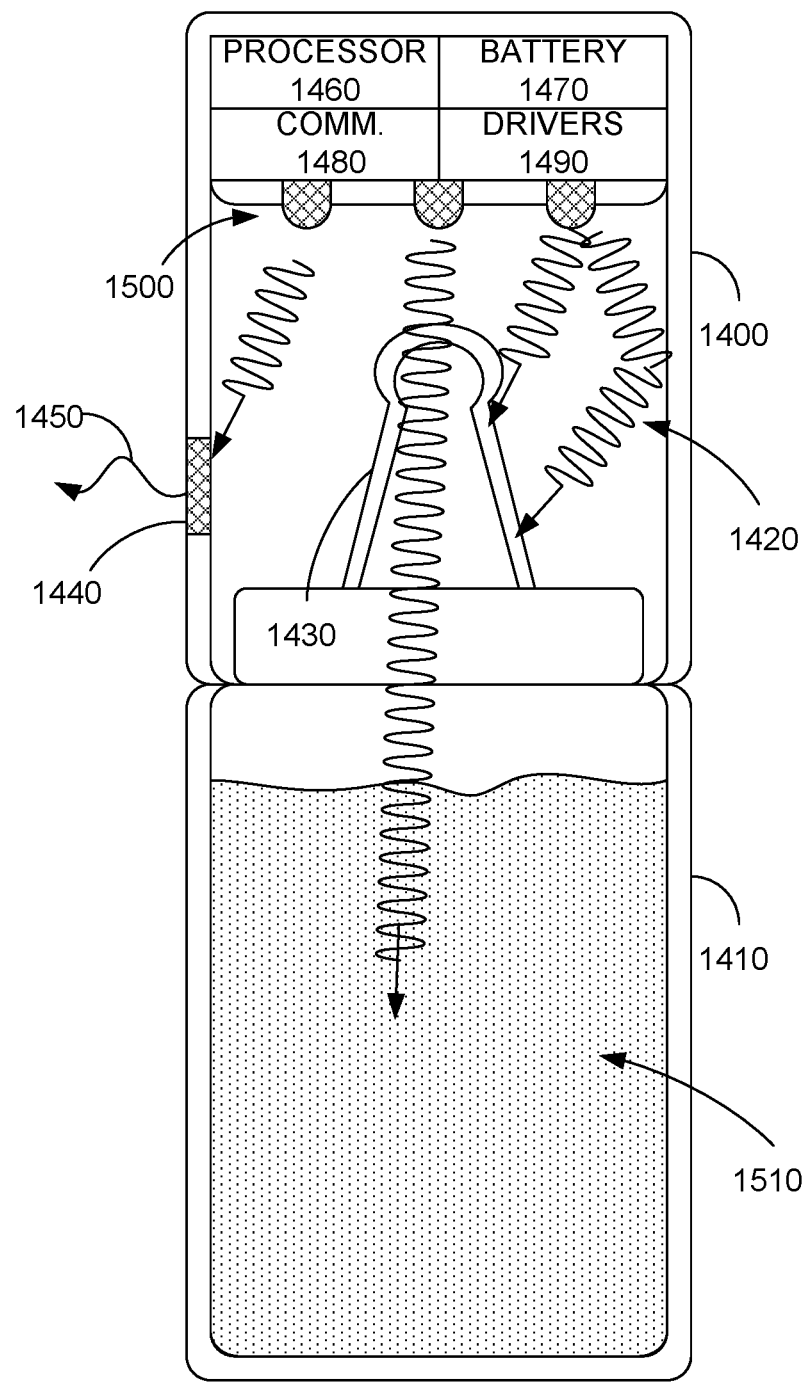
FIG. 13 illustrates an embodiment of the present invention.

FIG. 13 illustrates another embodiment of the present invention. In FIG. 13, a UV portion 1400 may be disposed above a bottle 1410, and provide UV light 1420 to the liquid 1510, as well as a liquid consumption structure 1430 (e.g. nipple, spout, straw, etc.). Similar to the embodiment in FIG. 5, in one embodiment, UV portion 1400 may include a UV sensitive region 1440 that emits visible light 1450 when struck by UV light 1420. In other embodiments, a visible light LED or the like may be provided within UV portion 1400 to visually indicate when UV light 1420 is being produced. In some embodiments, UV portion 1400 may also include a processor 1460, a power supply 1470, a communications portion 1480, UV LEDs 1500, and LED drivers 1490, having similar functionality described above.

The block diagrams of the architecture and flow charts are grouped for ease of understanding. However it should be understood that combinations of blocks, additions of new blocks, re-arrangement of blocks, and the like are contemplated in alternative embodiments of the present invention.

The specification and drawings are, accordingly, to be regarded in an illustrative rather than a restrictive sense. It will, however, be evident that various modifications and changes may be made thereunto without departing from the broader spirit and scope of the invention as set forth in the claims.

The invention claimed is:

1. A liquid treatment device comprising:
    a UV-LED module configured to provide UV-B or UV-C band light to liquid;
    a plurality of LEDs configured to provide visible light;
    a base housing comprising a first UV transmissive material disposed on a portion of the base housing adjacent to the UV-LED module; and
    a liquid storage portion comprising a second UV transmissive material, wherein the second UV transmissive material is configured to allow the UV-B or UV-C band light from the UV-LED module to be transmitted into the liquid.

2. The liquid treatment device of claim 1, further comprising a user output portion coupled to the liquid storage portion, wherein the user output portion is configured to restrict outflow of the liquid from the liquid storage portion, and wherein the user output portion is selected from a group consisting of: a lid, a screw-on cap, a flip-top cap, a flap, a nipple.

3. The liquid treatment device of claim 1, wherein the base housing further comprises a power source, a processor and a communication module coupled to the power source and to the processor, wherein the communication module is configured to provide usage data to a remote device.

4. The liquid treatment device of claim 1, wherein the base housing further comprises a power source, a processor and a pressure sensor coupled to the power source and to the processor, wherein the pressure sensor is configured to determine weight of the liquid storage portion upon the base housing.

5. The liquid treatment device of claim 1, wherein the first UV transmissive material is configured to allow the UV-B or UV-C band light from the UV-LED module to be transmitted outward from the base housing.

6. The liquid treatment device of claim 1, further comprising a liquid storage housing removably couplable to the portion of the base housing, wherein the liquid storage housing comprises the liquid storage portion configured to hold the liquid.

7. The liquid treatment device of claim 1, further comprising
    a processor electrically coupled to a power source, the UV-LED module, and to the plurality of LEDs,
    wherein the processor is configured to specify parameters for power from the power source to the UV-LED module, and wherein the processor is further configured to specify parameters for power from the power source to the plurality of LEDs.

8. The liquid treatment device of claim 6, wherein the liquid storage housing is configured as a baby bottle; and wherein the base housing further comprises a cradle adapted to interface with the baby bottle.

9. The liquid treatment device of claim 6, wherein the liquid storage housing further comprises a mechanical agitator.

10. The liquid treatment device of claim 6, wherein the base housing is disposed on top of the liquid storage housing or below the liquid storage portion.

11. A method for treating milk comprising:
    filling a milk container with milk, wherein the milk container includes
        a UV-LED module configured to provide UV-B or UV-C band light to liquid;
        a plurality of LEDs configured to provide visible light;
        a base housing comprising a first UV transmissive material disposed on a portion of the base housing adjacent to the UV-LED module; and
        a liquid storage portion comprising a second UV transmissive material, wherein the second UV transmissive material is configured to allow the UV-B or UV-C band light from the UV-LED module to be transmitted into the milk.

12. The method of claim 11, further comprising:
    providing the milk to a user via a user output portion of the milk container,
        wherein the user output portion is configured to restrict outflow of the milk from the milk container; and
        wherein the user output portion is selected from a group consisting of: a nipple, a straw, and a spout.

13. The method of claim 12, further comprising:
    determining with a pressure sensor in the base housing, a first weight of the milk container, prior to providing the milk to the user;
    determining with the pressure sensor in the base housing, a second weight of the milk container, after providing the milk to the user; and
    determining with a processor in the base housing, an approximate consumption amount of the milk.

14. The method of claim 13, further comprising: transmitting the approximate consumption amount to a remote device, wherein the remote device is selected from a group consisting of: a smart device, a remote server.

15. The method of claim 11, further comprising: transmitting an indication to a remote device that the UV-B or UV-C band light has been provided to the milk in the milk container, wherein the remote device is selected from a group consisting of: a smart device, a remote server.

16. The method of claim 11, further comprising agitating the milk, wherein the agitating the milk comprises a user manually agitating the milk container.

17. The method of claim 11, further comprising agitating the milk, wherein the agitating the milk comprises activating an agitator in the milk container; and wherein the agitator is selected from a group consisting of: a stirring mechanism and a bubbler mechanism.

18. The method of claim 11, further comprising periodically using a processor in the base housing to provide operating power to the UV-LED module to thereby provide the UV-B or UV-C band light to the milk in the milk container.

19. The method of claim 11, further comprising: determining with an opacity sensor in the base housing an opacity of the milk; and using a processor in the base housing to provide operating power to the UV-LED module in response to the opacity of the milk.

20. The method of claim 11, wherein the milk container comprises a baby bottle; and further comprising coupling the milk container to the base housing, wherein the coupling the milk container to the base housing comprises placing the baby bottle upon a top surface of the base housing.

* * * * *